United States Patent [19]

Meguro et al.

[11] Patent Number: 4,725,610

[45] Date of Patent: Feb. 16, 1988

[54] THIAZOLIDINEDIONE DERIVATIVES, THEIR PRODUCTION AND USE

[75] Inventors: Kanji Meguro, Nishinomiya; Takeshi Fujita, Takarazuka, both of Japan

[73] Assignee: Takeda Chemical Industries, Ltd., Osaka, Japan

[21] Appl. No.: 783,628

[22] Filed: Oct. 3, 1985

[30] Foreign Application Priority Data

Oct. 3, 1984 [WO] PCT Int'l Appl. .... PCT/JP84/00466
Apr. 9, 1985 [WO] PCT Int'l Appl. .... PCT/JP85/00179

[51] Int. Cl.⁴ .................. C07D 417/12; A61K 31/425
[52] U.S. Cl. ...................................... 514/369; 514/342; 546/280; 548/183
[58] Field of Search ............... 548/183; 514/369, 342; 546/280

[56] References Cited

U.S. PATENT DOCUMENTS

4,287,200 9/1981 Kawamatsu et al. ............... 424/270
4,572,912 2/1986 Yoshioka et al. ................... 548/183

FOREIGN PATENT DOCUMENTS

0084926 8/1983 European Pat. Off. ............ 548/183

OTHER PUBLICATIONS

Sohda et al., *Chem. Pharm. Bull.*, vol. 32(6), pp. 2267–2278, (1984).

Shoda et al., *Chem. Pharm. Bull.*, 30(10), 3580–3600, (1982).
Shoda et al., *Chem. Pharm. Bull.*, 30(10), 3563–3573, (1982).
Fujita et al., *Diabetes*, vol. 32, 804–810, (1983).

*Primary Examiner*—Robert Gerstl
*Attorney, Agent, or Firm*—Wenderoth, Lind & Ponack

[57] ABSTRACT

Thiazolidinedione derivatives of the general formula:

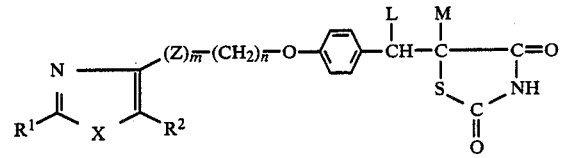

[wherein $R^1$ is hydrogen or a hydrocarbon residue or heterocyclic residue which may each be substituted; $R^2$ is hydrogen or lower alkyl which may be substituted by hydroxyl group; X is an oxygen or sulfur atom; Z is a hydroxylated methylene or carbonyl; m is 0 or 1; n is an integer of 1 to 3; L and M represent independently a hydrogen atom or L and M combine with each other to cooperate jointly to form a linkage] and their salts, which are novel compounds, possess blood-glucose and blood-lipid lowering actions in mammals, and are of value as a therapeutic agent for diabetes and therapeutic agent for hyperlipemia.

12 Claims, No Drawings

THIAZOLIDINEDIONE DERIVATIVES, THEIR PRODUCTION AND USE

This invention relates to novel thiazolidinedione derivatives which possess blood-glucose and blood-lipid lowering actions, to processes for producing the same and to pharmaceutical compositions containing the same.

As a therapeutic agent for diabetes, heretofore, there have been used various biguanide and sulfonylurea compounds. However, the biguanide compounds are hardly in current use, because they cause lactic acid acidosis, while the sulfonylurea compounds exhibit potent hypoglycemic action but often bring about severe hypoglycemia, thus requiring careful precautions on the occasion of their use. The development of a novel therapeutic agent for diabetes which is free from such defects is desired. In Japanese Unexamined Patent Publication Nos. 22636/1980 and 64586/1980, Chemical & Pharmaceutical Bulletin, 30, 3563 (1982), ibid. 30, 3580 (1982) and ibid., 32, 2267 (1984), on the other hand, there is a description that various thiazolidinediones exhibit blood-lipid and blood-glucose lowering actions, and in Diabetes, 32, 804 (1983), futhermore, there has been provided a description of the antidiabetic action demonstrated by ciglitazone. Nevertheless, all of these compounds has failed so far to be commercialized as a therapeutic agent for diabetes. The present inventors conducted repeated research on thiazolidinediones, and as a result, found entirely novel derivatives which possess outstandingly potent blood-glucose and blood-lipid lowering actions and can be expected to provide enhanced therapeutic effect, as compared with the known compounds.

This invention is concerned with:

1. A thiazolidinedione derivative of the general formula:

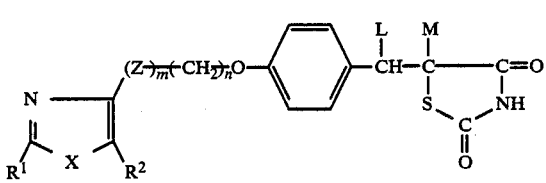

[wherein $R^1$ is hydrogen or a hydrocarbon residue or heterocyclic residue which may each be substituted; $R^2$ is hydrogen or a lower alkyl group which may be substituted by hydroxyl group; X is an oxygen or sulfur atom; Z is a hydroxylated methylene or carbonyl; m is 0 or 1; n is an integer of 1 to 3; L and M represent independently a hydrogen atom or L and M combine with each other to cooperate jointly to form a linkage] or its pharmacutically acceptable salts, 2. A pharmaceutical composition which contains a compound of the general formula (I) or its pharmacutically acceptable salt, 3. A process for producing a compound of the general formula:

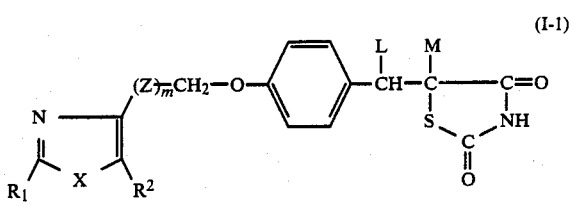

[wherein each of the symbols is as defined hereinbefore] or its salt, which comprises reacting a compound of the general formula:

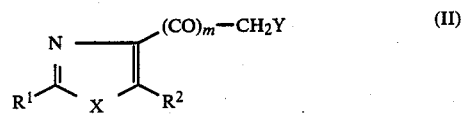

[wherein $R^1$, $R^2$, X and m are as defined hereinbefore; Y is a halogen atom] with a compound of the general formula:

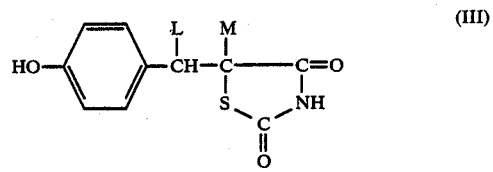

[wherein each of the symbols is as defined hereinbefore] or its salt, followed by reduction of the reaction product, if desired, 4. A process for producing a compound of the general formula:

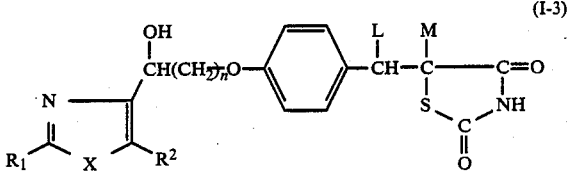

[wherein each of the symbols is as defined hereinbefore] or its salt, which comprises reducing a compound of the general formula:

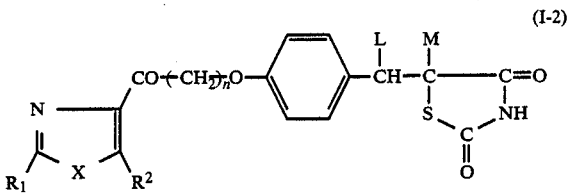

[wherein each of the symbols is as defined hereinbefore] or its salt,

5. A process for producing a compound of the general formula (I-2) or its salt, which comprises oxidizing a compound of the general formula (I-3) or its salt, 6. A process for producing a compound of the general formula:

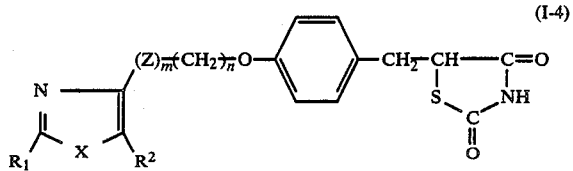

[wherein each of the symbols is as defined hereinbefore] or its salt, which comprises hydrolyzing a compound of the general formula:

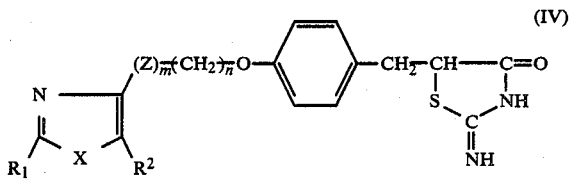

[wherein each of the symbols are as defined hereinbefore] or its salt,

7. A process for producing a compound of the general formula:

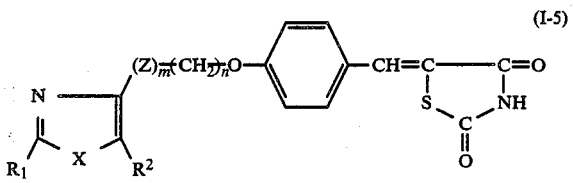

[wherein each of the symbols is as defined hereinbefore] or its salt, which comprises reacting a compound of the general formula:

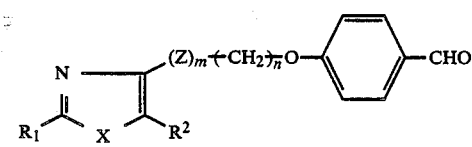

[wherein each of the symbols is as defined hereinbefore] with a compound of the formula:

or its salt,

8. A process for producing a compound of the general formula (I-4) or its salt, which comprises reducing a compound of the general formula (I-5) or its salt, and 9. A method for the treatment of diabetes or hyperlipemia, which comprises administering to a mammal suffering from the disease a compound of the formula (I) or its pharmaceutically acceptable salt, in amount of about 0.001 to 10 mg per kilogram of body weight of the mammal per day.

In the above general formulae (I), (I-1), (I-2), (I-3), (I-4), (I-5), (II), (III), (IV) and (V), the hydrocarbon residue represented by $R^1$ is that having 1 to 13 carbon atoms and includes aliphatic hydrocarbon residues, alicyclic hydrocarbon residues, alicyclic aliphatic hydrocarbon residues, aromatic-aliphatic hydrocarbon residues and aromatic hydrocarbon residues. The said aliphatic hydrocarbon residue is that having 1 to 8 carbon atoms and includes saturated aliphatic hydrocarbon residues of 1 to 8 carbon atoms, such as methyl, ethyl, propyl, isopropyl, butyl, isobutyl, sec-butyl, t-butyl, pentyl, isopentyl, neopentyl, t-pentyl, hexyl, isohexyl, heptyl and octyl, and unsaturated aliphatic hydrocarbon residues of 2 to 8 carbon atoms, such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-1-2-butenyl, 1-hexenyl, 3-hexenyl, 2,4-hexadienyl,5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl; the said alicyclic hydrocarbon residue is that having 1 to 8 carbon atoms and includes saturated alicyclic hydrocarbon residues of 3 to 7 carbon atoms, such as cyclopropyl, cyclobutyl, cyclopentyl, cyclohexyl and cycloheptyl, and unsaturated alicyclic hydrocarbon residues of 5 to 7 carbon atoms, such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl; the alicyclic-aliphatic hydrocarbon residue is that consisting of the above-described alicyclic hydrocarbon residues bonded to the above-mentioned aliphatic hydrocarbon residues but having 4 to 9 carbon atoms, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl; and the aromatic-aliphatic hydrocarbon residue is that having 7 to 13 carbon atoms and includes phenylalkyls of 7 to 9 carbon atoms, such as benzyl, phenethyl, 1-phenylethyl, 3-phenylpropyl, 2-phenylpropyl and 1-phenylpropyl, and naphthylalkyls of 11 to 13 carbon atoms, such as α-naphthylmethyl, α-naphthylethyl, β-naphthymethyl and β-naphthylethyl, while the aromatic hydrocarbon residue includes for example, phenyl and naphthyls (α-naphthyl and β-naphthyl). The heterocyclic residue represented by $R^1$ denotes five-membered or six-membered rings containing, in addition to carbon, 1 to 3 atoms selected from N, O and S as a ring-forming atom and capable of bonding through carbon, and their specific examples include heteroaromatic ring groups, such as thienyls (2-thienyl, 3-thienyl), furyls (2-furyl, 3-furyl), pyridyls (2-pyridyl, 3-pyridyl, 4-pyridyl), thiazolyls (2-thiazolyl, 4-thiazolyl, 5-thiazolyl) and oxazolyls (2-oxazolyl, 4-oxazolyl, 5-oxazolyl), and saturated heterocyclic groups, such as piperidinyls (2-piperidinyl, 3-piperidinyl, 4-piperidinyl), pyrrolidinyls (2-pyrrolidinyl, 3-pyrrolidinyl), morpholinyls (2-morpholinyl, 3-morpholinyl) and tetrahydrofuryls (2-tetrahydrofuryl, 3-tetrahydrofuryl). The hydrocarbon residue and heterocyclic residue represented by $R^1$ may have a substituent or substituents in their arbitrary positions. In cases in which $R^1$ includes an a alicyclic group or $R^1$ is a saturated heterocyclic group, such groups may have 1 to 3 lower alkyl groups (e.g., methyl, ethyl, propyl, isopropyl) of 1 to 3 carbon atoms on their rings (inclusive of the N atom). In cases in which $R^1$ includes a aromatic hydrocarbon group or $R^1$ is a hetero-aromatic ring group, such groups may have 1 to 4 of the same or different substituents on their rings (exclusive of the hetero atoms), whereby the said substituents include, for example, halogens (e.g., fluorine, chlorine, iodine), hydroxyl, cyano, trifluoromethyl, lower alkoxies (e.g., those having 1 to 4 carbon atoms, such as methoxy, ethoxy, propoxy, isopropoxy and butoxy), lower alkyls (e.g., those having 1 to 4 carbon atoms, such as methyl, ethyl, propyl, isopropyl and butyl), lower alkoxycarbonyls (e.g. those having 2 to 4 carbon atoms such as methoxycarbonyl, ethoxycarbonyl, propoxycarbonyl, etc.) and lower alkylthios (e.g., those having 1 to 3 carbon atoms, such as methylthio, ethylthio, propylthio and isopropylthio).

The lower alkyl group represented by $R^2$ includes those having 1 to 5 carbon atoms, such as methyl, ethyl, propyl, isopropyl, butyl, isobutyl, sec-butyl, t-butyl and pentyl, whereupon those having 1 to 4 carbon atoms are preferred and those having 1 to 3 carbon atoms are the most preferable. These alkyl groups may have a hydroxyl group or hydroxyl groups in their arbitrary positions, with the α position being particularly preferable.

In the general formulae (I), (I-1), (I-2), (I-3) and (III), when L and M combine with each other and cooperate jointly to form a linkage, this is understood to mean that the carbon atoms at both ends of this linkage combine with each other through the double bond. In cases in which L and M combine with each other and cooperate jointly to form a linkage, the compound of the general formula (I), for example, is represented by the general formula (I-5). In cases in which L and M represent independently a hydrogen atom, the compound of the general formula (I) is represented by the general formula (I-4).

The halogen represented by Y in the general formula (II) includes chlorine, bromine and iodine.

The compound of the general formula (I), which has acid nitrogen on its thiazolidine ring, forms salts with bases. Such base salts include pharmaceutically acceptable salts, such as sodium salt, potassium salt, aluminum salt, magnesium salt and calcium salt.

The compound of the general formula (I) or its salts can be produced by the following procedure.

The compound of the general formula (I) wherein n is 1 or its salts, namely the compound represented by the general formula (I-1) or its salts [hereinafter referred to collectively as "Compound (I-1)"] can be formed by reacting a compound of the general formula (II) with a compound of the general formula (III) or its salt [hereinafter referred to collectively as "Compound (III)"], followed by reduction of the reaction product, if desired. The reaction of Compound (II) with Compound (III) is normally carried out in the presence of suitable solvent and base, and this reaction can afford the compound (I'), namely the desired compound (I) with m=0 and n=1.

Examples of such a solvent include dimethylformamide, dimethylsulfoxide, tetrahydrofuran, dimethoxyethane, etc., while examples of the said base include sodium hydride, potassium hydride, sodium amide, sodium alkoxides (e.g., sodium methoxide, sodium ethoxide), potassium alkoxides (e.g., potassium butoxide). This reaction is preferably carried out by firstly reacting 1 mole of Compound (II) with 2 moles of a base to form a dianion and subsequently adding 1 mole of Compound (II) to allow the reaction to proceed. This condensation reaction is conducted normally at 0° C. to 120° C., preferably at 20° C. to 100° C., and the reaction time is normally 0.5 to 5 hours.

In this reaction, the use of the compound of the general formula (II) wherein m=1 as a starting compound can produce Compound (I-1) wherein m is 1 and Z is carbonyl. This compound, when subjected to reduction, if desired, can be converted into Compound (I-1) wherein m is 1 and Z is

The compound of the general formula (I-2) or its salts [hereinafter referred to collectively as "Compound (I-2)"] can be converted through reduction into the compound of the general formula (I-3) or its salts [hereinafter referred to collectively as "Compound (I-3)"]. This reduction reaction can be allowed to proceed readily by utilizing sodium borohydride in a solvent such as an alkanol (e.g. methanol, ethanol, 2-propanol, 2-methoxyethanol), if desired, admixed with N,N-dimethylformamide. The amount of sodium borohydride to be used is 0.3 to 2 moles per mole of Compound (I-2). The reaction temperature is −10° C. to 100° C., while the reaction time is 0.5 to 5 hours.

Compound (I-3) can be converted through oxidation into Compound (I-2). This oxidation reaction can be allowed to proceed readily by means of activated DMSO oxidation utilizing dimethylsulfoxide (DMSO) and an electrophilic reagent (e.g., acetic anhydride, dicyclohexylcarbodiimide (DCC), phosphorus pentaoxide, etc.), by chromic acid oxidation.

The activated DMSO oxidation can be allowed to proceed by adding an electrophilic reagent, such as acetic anhydride, DCC and phosphorus pentoxide, in DMSO, if desired, admixed with benzene, pyridine, ether, etc. The amount of DMSO to be used is normally in large excess, and the reaction temperature ranges from −10° C. to 60° C., preferably from 0° to 30° C., varying depending upon the type of the electrophilic reagent to be used, while the reaction time is 1 to 30 hours. The chromic acid oxidation can be allowed to proceed by means of the methods of utilizing a Jones reagent (chromium trioxide-sulfuric acid-acetone) in chromium trioxide in acetic acid, chromium trioxide in pyridine or a previously prepared chromium trioxidepyridine complex in dichloromethane used as a solvent. The amount of chromium (VI) to be used is normally 0.5 to 2 equivalents against Compound (I-3). The reaction temperature is −10° C. to 60° C., preferably 0° to 30° C., while the reaction time is 0.5 to 50 hours.

The compound of the general formula (I) wherein L and M both are independently a hydrogen atom or its salts, namely the compound of the general formula (I-4) or its salts (hereinafter referred to collectively as "Compound (I-4)"), can be produced by hydrolyzing a compound of the general formula (IV) or its salts (hereinafter referred to collectively as "Compound (IV)"). This hydrolysis reaction is carried out normally in a suitable solvent in the presence of water and mineral acid. As the solvent, there are mentioned normally alkanols (e.g., methanol, ethanol, propanol, 2-propanol, butanol, isobutanol, 2-methoxyethanol, etc.), dimethylsulfoxide, sulfolane, dioxane, dimethoxyethane, etc. The mineral acid includes, for example, hydrochloric acid, hydrobromic acid, sulfuric acid, etc., and their amount to be used is 0.1 to 10 moles per mole of the compound (IV), preferably 0.2 to 3 moles. The amount of water to be added is normally in large excess per mole of the compound (IV). This reaction is normally conducted under warming or heating, and the reaction temperature is ordinarily 60° to 150° C. The reaction time is nomally several hours to ten-odd hours.

The compound of the general formula (I-5) or its salts [hereinafter referred to collectively as "Compound (I-5)"] can be produced by reacting a compound of general formula (V) with a compound of the formula (VI) or its salt [hereinafter referred to collectively as "Compound (VI)"]. This reaction is carried out normally in a solvent in the presence of a suitable base. As such a solvent-base system, there are used systems being suitably selected from solvents, such as alkanols (e.g., methanol, ethanol, propanol, 2-propanol, butanol, isobutanol, 2-methoxyethanol, etc.), dimethylformamide, dimethylsulfoxide, sulfolane, acetonitrile, dioxane, dimethoxyethane and acetic acid, and bases, such as amines (e.g., pyrrolidine, piperidine, morpholine, piperazine, diethylamine, diisopropylamine, triethylamine, etc.), sodium alkoxides (e.g., sodium methoxide, sodium ethoxide), potassium carbonate, sodium carbonate, sodium hydride, sodium acetate and potassium acetate. Compound (VI) is used normally at a rate of 1 to 5 mole per mole of the compound of the general formula (V), preferably 1.5 to 3.0 moles. The amount of the base to be used is 0.01 to 3.0 moles per mole of the compound (VI), preferably 0.1 to 1.0 mole. This condensation reaction is carried out normally at 0° C. to 150° C., preferably 20° C. to 100° C., while the reaction time is normally 0.5 to 50 hours.

Compound (I-4) can be produced by reducing Compound (I-5). This reaction is carried out normally by catalytic hydrogenation in a solvent in the presence of a suitable catalyst. As the solvent, there are mentioned normally alkanols (e.g. methanol, ethanol, propanol, etc.), ethers (e.g. dioxane, dimethoxyethane, tetrahydrofuran, etc.), ethyl acetate, acetic acid, dimethylformamide, etc. The catalyst includes, for example, palladium black, palladium carbon, platinum oxide, etc. This reaction can proceed at an ordinary temperature and pressure, but may be carried out at an elevated temperature (about 40° to 100° C.) and pressure in order to accelerate the reaction.

The compound of the general formula (I) wherein $R^2$ is an alkyl group having a hydroxyl group in the α-position or its salts can also be produced for example by the procedure to be described in the following:

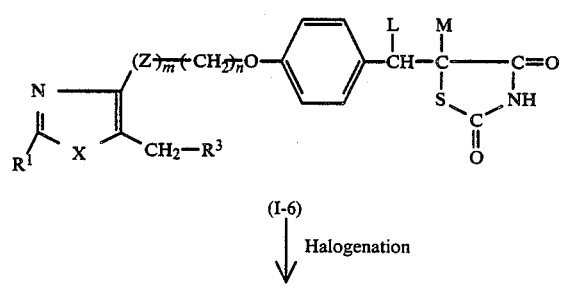

(I-6)

↓ Halogenation

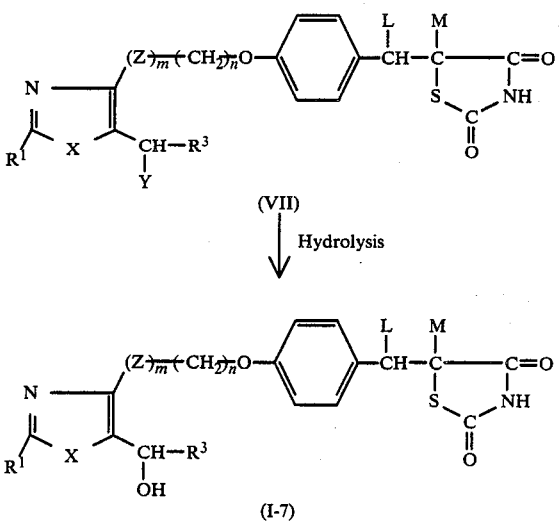

[wherein $R^3$ is hydrogen or a lower alkyl group (e.g., methyl, ethyl, propyl, isopropyl, butyl, isobutyl, etc.); each of the other symbols is as defined hereinbefore].

Namely, the compound (I-6), that is the compound (I) wherein $R^2$ is lower alkyl represented by $CH_2-R^3$, or its salts [hereinafter referred to collectively as Compound (I-6)"], when halogenated, affords the compound of the general formula (VII) or its salts [hereinafter referred to collectively as "Compound (VII)]. Compound (VII) is then converted into the objective compound (I-7) or its salts [hereinafter referred to collectively as "Compound (I-7)] by hydrolysis. The halogenation of Compound (VII) can be carried out with N-bromosuccinimide or N-chlorosuccinimide, preferably in the presence of a radical initiator, such as benzoyl peroxide and α,α'-azobisisobutyronitrile. This reaction is allowed to proceed readily by refluxing in a solvent, such as carbon tetrachloride and chloroform, and the amount of the radical initiator to be used is normally 0.01 to 0.2 mole per mole of Compound (I-6). The resulting α-halogenated derivative [Compound (VII)] may be hydrolyzed, after being isolated and purified, if necessary, or directly without isolation to the α-hydroxy derivative [Compound (I-7)]. This hydrolysis reaction is allowed to proceed advantageously by using a mineral acid in a suitable solvent. As the solvent, there are used dioxane, tetrahydrofuran, dimethoxyethane, etc., while as the mineral acid, there are used hydrochloric acid, sulfuric acid, etc., respectively, and the reaction temperature is 20° C. to 100° C., with the reaction time ranging from 0.5 to 10 hours.

The thiazolidinedione derivative (I) and its salts as obtained in this manner can be isolated and purified by the known separation and purification means, such as concentration, concentration under reduced pressure, solvent extraction, crystallization, recrystallization, phase-transfer and chromatography.

The compound (I) of this invention and its salt exhibit excellent blood-glucose and blood-lipid lowering actions in mammals (e.g., mouse, rat, dog, cat, monkey, horse, and human being), and show a low degree of toxicity in terms of both acute and subacute toxicities. Therefore, the thiazolidinedione derivative (I) and its salts is of value to human beings for the treatment of hyperlipemia, diabetes and their complications. With reference to the method of administration, they are normally used orally in such dosage forms as tablets, capsules, powders, granules, etc., and can also be administered parenterally in dosage forms, such as injectable solutions, suppositories and pellets, as the case may be. In the case of application as a therapeutic agent for diabetes or hyperlipemia, the compounds can be normally administered to an adult patient orally at a dose of 0.003 to 10 mg/kg a day, preferably 0.01 to 10 mg/kg, most preferably 0.02 to 0.2 mg/kg, or parenterally at a dose of 0.001 to 10 mg/kg a day, preferably 0.005 to 10 mg/kg, most preferably 0.01 to 0.1 mg/kg, whereby such doses are desirably given once a day or twice to four times a week intermittently.

The starting compound (V) of this invention can be produced, for example, by the following procedure.

(1a) Preparation of the compound (V-1), i.e. compound (V) wherein m=0.

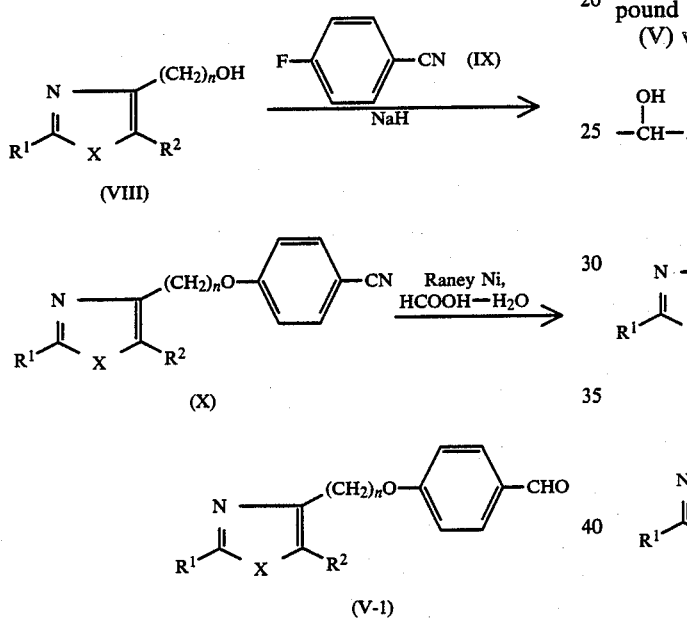

[wherein each of the symbols is as defined hereinbefore].

The reaction of the compound (VIII) to the compound (X) is carried out by allowing the compounds (VIII) and (IX) to undergo condensation for example in the presence of sodium hydride. This reaction can be conducted in a solvent, such as dimethylformamide, dimethylsulfoxide, tetrahydrofuran and dimethoxyethane, at $-10°$ C. to $30°$ C. The subsequent reaction of the compound (X) to the compound (V-1) is carried out by heating the compound with Raney nickel alloy in an aqueous formic acid solution.

(1b) Production of the compound (V-2) of the general formula (V) wherein m=0 and n=1, or m=n=1 and Z=—CO—.

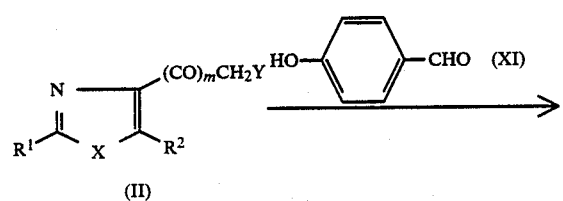

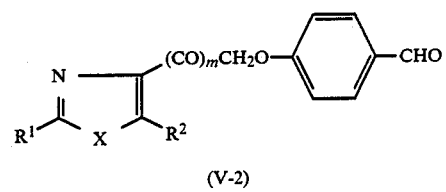

[wherein each of the symbols is as defined hereinbefore].

The reaction of condensation of the compound (II) with the compound (XI) to give (V-2) is normally allowed to proceed in a solvent, such as dimethylformamide, tetrahydrofuran, acetone and methyl ethyl ketone, in the presence of a base (e.g., sodium carbonate, potassium carbonate, etc.) at $0°$ C. to $150°$ C.

(1c) Preparation of the compound (V-3), i.e. compound (V) wherein m=n=1 and Z=

$$\begin{array}{c} \text{OH} \\ | \\ -\text{CH}- \end{array}$$

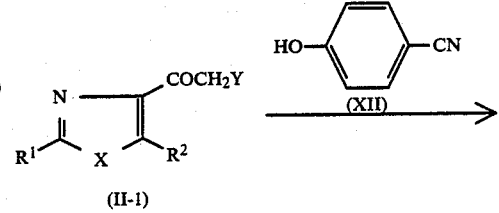

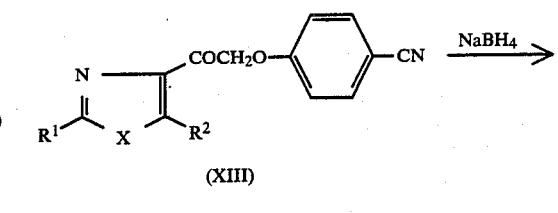

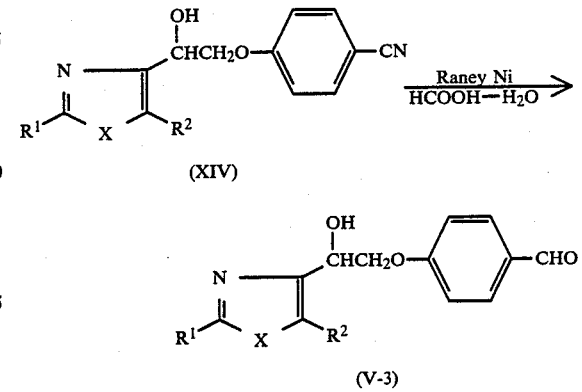

[wherein each of the symbols is as defined hereinbefore].

The reaction of the compound (II-1) with the compound (XII) can be carried out in a manner similar to the above-described reaction between the compounds (II) and (XI), and the resulting compound (XIII) is reduced in accordance with the conventional procedure by use of sodium borohydride in a solvent such as methanol, ethanol, and N,N-dimethylformamide, or their mixture to give the compound (XIV), which can subsequently be converted to (V-3) by a reaction similar to the above-described reaction of converting (X) into (V-1).

(2a) Preparation of the compound (IV-1), i.e. compound (IV) wherein m=0.

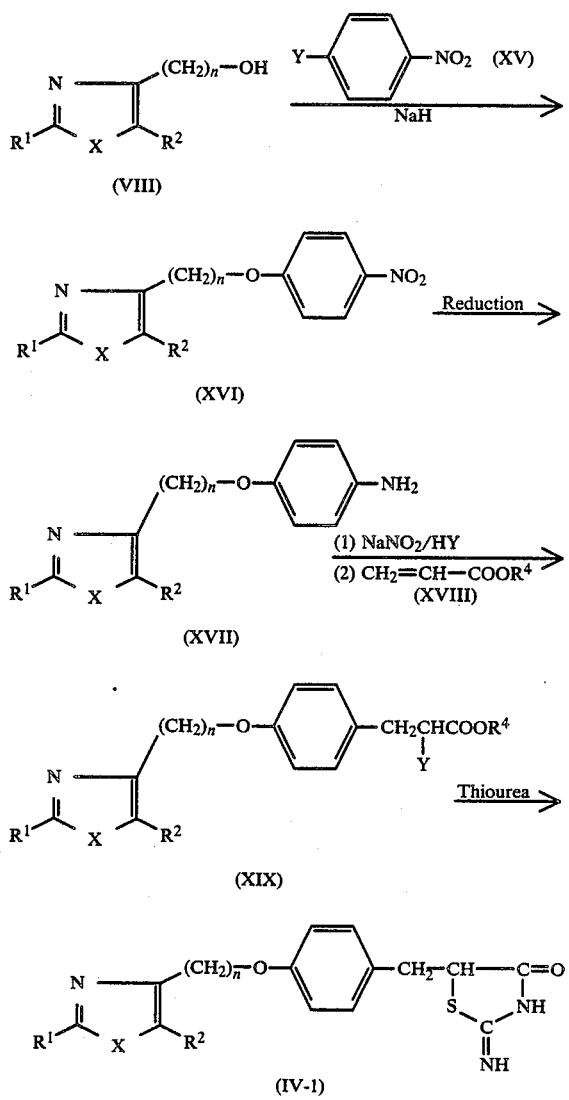

(IV-1)

[wherein $R^4$ is hydrogen or a lower alkyl group; other symbols are as defined hereinbefore].

The lower alkyl group represented by $R^4$ in the above general formulae (XVIII) and (XIX) includes alkyl groups of 1 to 4 carbon atoms, such as methyl, ethyl, propyl and butyl.

The reaction of the compound (VIII) to the compound (XVI) is carried out by condensation of the compound (VIII) with the compound (XV) for example in the presence of sodium hydride. This reaction can be conducted in a solvent, such as dimethylformamide and tetrahydrofuran, at −10° C. to 30° C. The subsequent reaction of the compound (XVI) to the compound (XVII) is readily carried out, for example, by catalytic reduction of the compound (XVI) in accordance with the conventional method by the use of palladium carbon as a catalyst or by reduction of the compound in accordance with the conventional method by the use of zinc or iron and acetic acid. The compound (XVII) may be isolated as a pure product or can be subjected to the reaction in the subsequent step without being isolated and purified. The reaction of the compound (XVII) to the compound (XIX) is carried out by means of the so-called Meerwein arylation reaction which involves diazotization of the compound (XVII) in the presence of a hydrohalogenic acid (HY), followed by reaction with acrylic acid or its ester (XVIII) in the presence of a copper catalyst (e.g., cuprous oxide, cupric oxide, cuprous chloride, cupric chloride, cuprous bromide, cupric bromide, etc.). The compound (XIX) can be purified by chromatography, and can also be subjected to the reaction in the subsequent step without being isolated and purified.

The compound (IV-1) can be produced by reacting thereafter the compound (XIX) with thiourea.

This reaction is carried out normally in a solvent, such as alcohols (e.g., methanol, ethanol, propanol, 2-propanol, butanol, isobutanol, 2-methoxyethanol, etc.), dimethylsulfoxide and sulfolane. The reaction temperature is normally 20° C. to 180° C., preferably 60° C. to 150° C. The amount of thiourea to be used is 1 to 2 moles per mole of the compound (XIX). This reaction proceeds with a hydrogen halide being formed as a by-product, and may be carried out in the presence of sodium acetate, potassium acetate, etc. for the purpose of capturing such a by-product. The amount of these compounds to be used is normally 1 to 1.5 moles per mole of the compound (XIX). This reaction can yield the compound (IV-1), which can be isolated, if desired, but may be subjected to the following hydrolysis step directly without being isolated.

The compound (XVII) having a hydroxy-substituted phenyl group as $R^1$ can be synthesized by condensation of the compound (VIII) having a benzyloxy-substituted phenyl group as $R^1$ with the compound (XV) and catalytic reduction of the resulting compound (XVI) to perform simultaneously reduction of the nitro group and debenzylation. Also, the compound (XVII) can be synthesized by the following procedure.

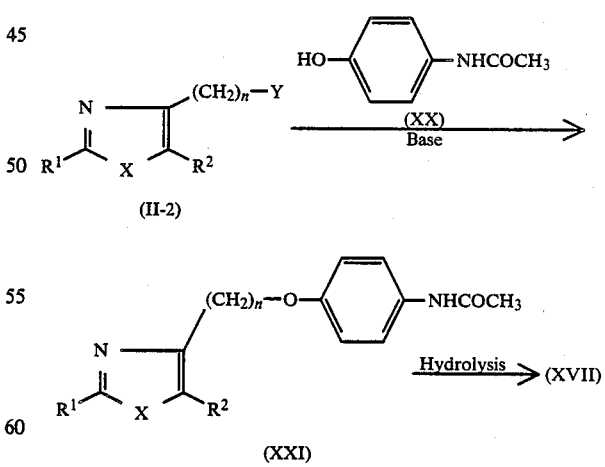

[wherein each of the symbols is as defined hereinbefore].

The condensation of the compound (II-2) with the compound (XX) to give the compound (XXI) can be normally conducted in a solvent, such as dimethylformamide, tetrahydrofuran, acetone and methyl ethyl ketone, in the presence of a base (e.g., sodium carbonate, potassium carbonate, etc.) at 0° C. to 150° C. Subsequently, (XXI) is hydrolyzed to the compound (XVII). This hydrolysis reaction can be carried out with a mineral acid (e.g., hydrochloric acid, hydrobromic acid, sulfuric acid, etc.) or more preferably with an alkali hydroxide (e.g., sodium hydroxide, potassium hydroxide, etc.) in a solvent, such as methanol, ethanol, propanol, 2-propanol and 2-methoxypropanol, under reflux.

(2b) Preparation of the compound (IV-2), i.e. compound (IV) wherein m=1.

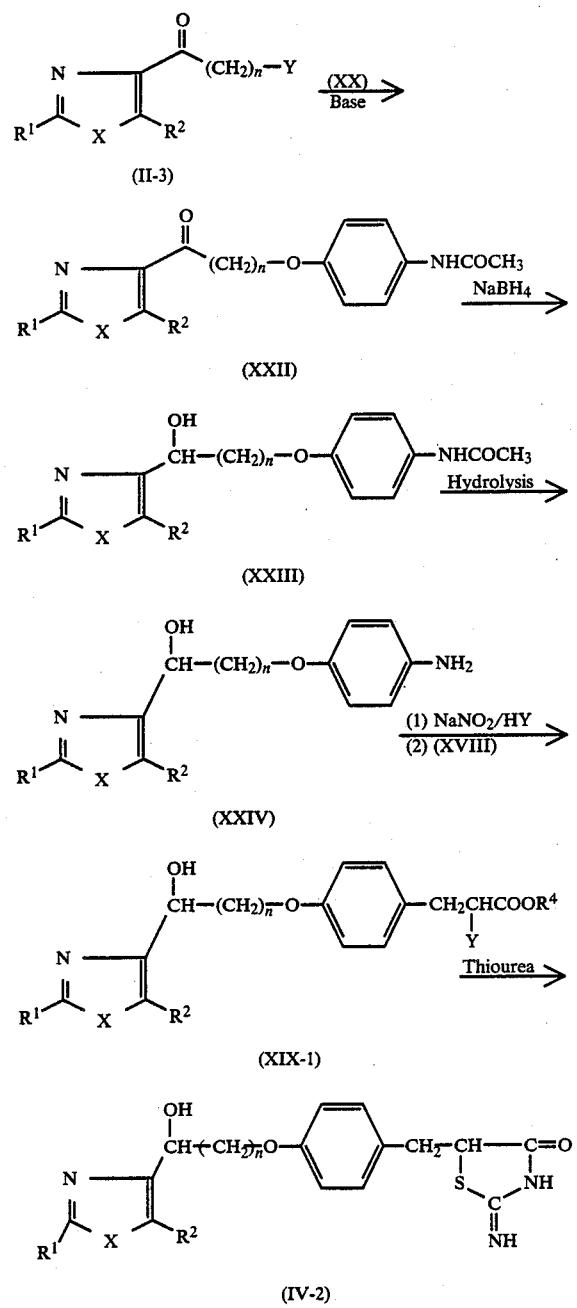

[wherein each of the symbols is as defined hereinbefore].

The condensation reaction of the compound (II-3) with the compound (XX) can be carried out in a manner similar to that of the above-mentioned reaction of the compound (II-2) with the compound (XX). The resulting compound (XXII) is reduced, by the conventional method, with sodium borohydride in methanol or ethanol to give the compound (XXIII), which then can be hydrolyzed, in a manner similar to that of the above hydrolysis of (XXI), to afford the compound (XXIV). By the same procedure as that used in producing (IV-1) from (XVII), the compound (XXIV) can be converted into (IV-2) through (XIX-1).

The starting materials (II) wherein m=0, can be prepared, for example, by the methods described in J. Am. Chem. Soc., 56, 470 (1934) and Japanese Unexamined Patent Publication No. 219169 (1983), or by the procedure analogous to them. Compounds (II-4), i.e. compound (II) wherein m=1, can be produced by the following method:

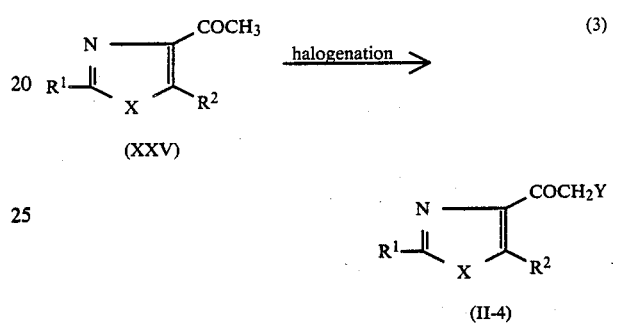

[wherein each of the symbols is as defined hereinbefore].

This reaction is performed by halogenating compounds (XXV) which can be produced, for example, by the methods described in Chem. Ber., 84, 96 (1951), Nihon Kagaku Zasshi, 86, 942 (1965), Bull. Soc. Chim. France, 9 3862 (1968), J. Chem. Soc., C., 1397 (1968) and German Pat. No. 2152557, or by the procedure analogous to them. The halogenation is conducted, for instance, with a halogen, preferably bromine, in a suitable solvent (e.g. chloroform, carbon tetrachloride) at 30°–60° C.

The starting compounds (VIII) for the preparation of the iminothiazolidine compounds (IV-1) are produced by the following methods.

(4a) Production of (VIII-1), i.e. compound (VIII) wherein n=2.

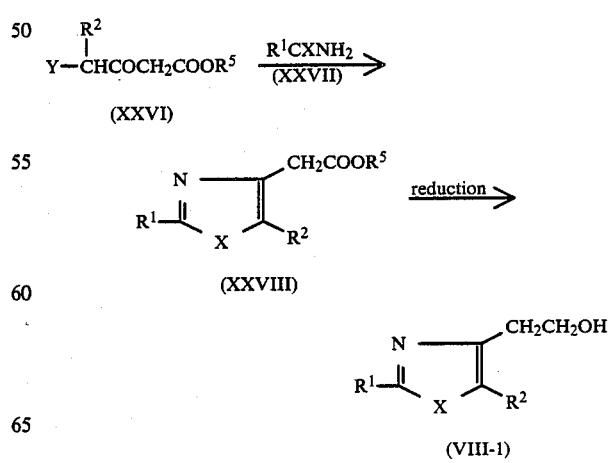

[wherein $R^5$ is a lower alkyl]

The reaction of (XXVI) which (XXVII) is easily conducted in a solvent such as an alkanol (e.g. methanol, ethanol, propanol, etc.), or without using a solvent, by heating at about 40°–150° C.

The resulting (XXVIII) is reduced by a conventional method, for example, using lithium aluminum hydride to yield (VIII-1). The compound (XXVIII) wherein x=0 is also prepared by the method described in Japanese Unexamined Patent Publication Nos. 201771 (1983) and 219169 (1983)/ or by the procedure analogous to them.

(4b) Compound (VIII) wherein n=1 can be prepared, for example, by the method described in Japanese Unexamined Patent Publication No. 219169 (1983), or by the procedure analogous to it.

The examples, reference examples and experiment examples are described below to illustrate this invention more specifically, but it is to be understood that this invention should not be limited to these examples.

EXAMPLE 1

To a solution of 5-(4-hydroxybenzyl)-2,4-thiazolidinedione (9.4 g) in N,N-dimethylformamide (80 ml) was added 60% sodium hydride in oil (3.4 g), and the mixture was stirred for 30 minutes. Then, a solution of 4-chloromethyl-2-phenyloxazole (9.6 g) in N,N-dimethylformamide (20 ml) was added dropwise thereto at room temperature. After being stirred at 70° C. for 1 hour, the reaction solution was poured into water, and the aqueous mixture was extracted with ethyl acetate. The ethyl acetate layer was washed with water, dried (MgSO$_4$) and concentrated to give 5-[4-(2-phenyl-4-oxazolylmethoxy)benzyl]-2,4-thiazolidinedione (9.1 g, 47.4%). Recrystallization from ethanol yielded colorless needles. m.p. 188°–189° C. Elemental analysis for $C_{20}H_{16}N_2O_4S$; Calcd.: C, 63.15; H, 4.24; N, 7.36. Found: C, 63.19; H, 4.16; N, 7.23.

EXAMPLES 2 TO 9

By a procedure similar to that of Example 1, there were obtained the compounds shown in Table 1.

TABLE 1

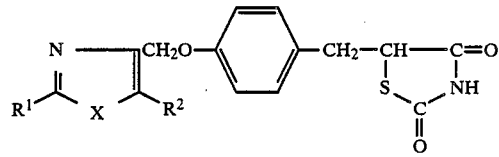

| Example No. | R$^1$ | R$^2$ | X | Melting point, °C. | Recrystallizing solvent | Yield % |
|---|---|---|---|---|---|---|
| 2 | phenyl | H | S | 164–165 | Acetone-hexane | 40.5 |
| 3 | C$_3$H$_7$— | H | O | 114–115 | Ethanol | 35.8 |
| 4 | CH$_3$ | H | S | 181–182 | Methanol-dichloromethane | 39.7 |
| 5 | CH$_3$ | H | O | 192–193 | Methanol-dichloromethane | 28.3 |
| 6 | phenyl | CH$_3$ | O | 162–163 | Ethyl acetate-hexane | 79.0 |
| 7 | 3-pyridyl | H | S | 205–206 | Methanol | 12.6 |
| 8 | 2-pyridyl | H | S | 209–211 | Methanol | 39.8 |
| 9 | benzyl (PhCH$_2$—) | CH$_3$ | O | 258–260 | Methanol | 28.9 |

EXAMPLE 10

60% sodium hydride in oil (1.32 g) was added to solution of 5-(4-hydroxybenzyl)-2,4-thiazolidinedione (3.35 g) in N,N-dimethylformamide (30 ml), and the mixture was stirred for 30 minutes. Then, solution of 4-chloromethyl-2-(1-methylcyclohexyl)oxazole (3.85 g) in N,N-dimethylformamide (5 ml) was added dropwise thereto at room temperature. After being stirred at 60° C. for 1 hour, the reaction solution was poured into water, and the aqueous mixture was extracted with ethyl acetate. The ethyl acetate layer was washed with water, dried (MgSO$_4$) and concentrated. The oily residue was chromatographed on a column of silica gel (70 g). Elution with hexaneethyl acetate (2:1, V/V) gave 5-{4-[2-(1-methylcyclohexyl)-4-oxazolylmethoxy]benzyl}-2,4-thiazolidinedione as an oily substance. A solution of sodium 2-ethylhexanoate in isopropanol (2N, 3 ml) was added to the oily substance, and treated with ether. The crystals which separated out were collected by filtration to give 5-{4-[2-(1-methylcyclohexyl)-4-oxazolylmethoxy]benzyl}-2,4-thiazolidinedione.sodium salt (2.3 g, 36.3%). Recrystallization from methanol afforded colorless plates. m.p. 285°–287° C. (decomp.) Elemental analysis for $C_{21}H_{23}N_2O_4SNa$, Calcd.: C, 59.70; H, 5.49; N, 6.63. Found: C, 59.76; H, 5.56; N, 6.82.

EXAMPLE 11

By a procedure similar to that of Example 10, there was obtained 5-[4-(1-cyclohexyl-4-thiazolylmethoxy)-benzyl]-2,4-thizaolidinedione sodium salt. Yield 20.4%. Recrystallization from methanol afforded colorless prisms. m.p. 298°–300° C. (decomp.) Elemental Analysis for $C_{20}H_{21}N_2O_3S_2Na$, Calcd.: C, 56.59; H, 4.99; N, 6.60. Found: C, 56.42; H, 5.02; N, 6.72

EXAMPLE 12

A mixture of 2-imino-5-{4-[2-(5-methyl-2-phenyl-4-oxazolyl)ethoxy]benzyl}-4-thiazolidinone (18.8 g), 2N-HCl (200 ml) and ethanol (200 ml) was heated under reflux for 12 hours. The solvent was distilled off under reduced pressure. The residue was neutralized with saturated aqueous solution of sodium hydrogen carbonate, and extracted with chloroform. The chloroform layer was washed with water and dried (MgSO4). The solvent was distilled off, whereby 5-{4-[2-(5-methyl-2-phenyl-4-oxazolyl)ethoxy]benzyl}-2,4-thiazolidinedione (18.0 g, 95.7%) was obtained. Recrystallization from ethanol afforded colorless needles. m.p. 113°–114° C. Elemental Analysis for $C_{22}H_{20}N_2O_4S$, Calcd.: C, 64.69; H, 4.93; N, 6.86. Found: C, 64.48; H, 4.91; N, 6.75.

EXAMPLES 13 TO 32

By a procedure similar to that of Example 12, there were obtained the compounds shown in Table 2.

TABLE 2

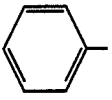

| Example No. | m | n | $R^1$ | $R^2$ | X | Melting point, °C. | Recrystallizing solvent | Yield % |
|---|---|---|---|---|---|---|---|---|
| 13 | 0 | 1 | 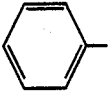 | H | O | 188–189 | Ethanol | 55.6 |
| 14 | 0 | 2 | CH₃ | H | S | 142–143 | methanol | 75.2 |
| 15 | 0 | 2 | CH₃ | H | O | 184–185 | Methanol-dichloromethane | 46.2 |
| 16 | 0 | 2 | 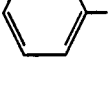 | H | S | 113–114 | Methanol | 90.8 |
| 17 | 0 | 2 |  | H | O | 109–110 | Ethyl acetate-hexane | 67.9 |
| 18 | 0 | 2 | CH₃ | CH₃ | O | 200–201 | Methanol-chloroform | 91.2 |
| 19 | 0 | 2 | C₃H₇ | H | O | 87–88 | Ether-hexane | 27.9 |
| 20 | 0 | 2 | C₂H₅ | H | S | 148–149 | Ethanol-dichloromethane | 84.3 |
| 21 | 0 | 2 | i-C₃H₇ | H | S | 107–108 | Ethyl acetate-hexane | 72.6 |
| 22 | 1 | 1 | 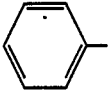 | CH₃ | O | 165–166 | Acetone-hexane | 51.5 |
| 23 | 0 | 2 |  | C₂H₅ | O | 109–111 | Ethyl acetate-hexane | 88.7 |

TABLE 2-continued

Structure: (CH)ₘ-(CH₂)ₙ-O-C₆H₄-CH₂ group attached to thiazolidinone with OH, N, R¹, X, R² substituents on oxazole ring.

| Example No. | m | n | R¹ | R² | X | Melting point, °C. | Recrystallizing solvent | Yield % |
|---|---|---|---|---|---|---|---|---|
| 24 | 0 | 2 | 4-CH₃O-C₆H₄- | CH₃ | O | 167–168 | Ethanol | 93.5 |
| 25 | 0 | 2 | CH₃ | C₂H₅ | O | 189–190 | Ethanol-chloroform | 90.1 |
| 26 | 0 | 2 | 2-furyl | CH₃ | O | 114–115 | Methanol | 52.1 |
| 27 | 0 | 2 | 2-thienyl | CH₃ | O | 144–145 | Methanol-dichloromethane | 60.0 |
| 28 | 1 | 1 | CH₃ | CH₃ | O | 214–215 | Ethanol-chloroform | 33.6 |
| 29 | 0 | 2 | 3-CH₃-C₆H₄- | CH₃ | O | 90–100 | Ethyl acetate-hexane | 83.1 |
| 30 | 0 | 2 | 2,3-(CH₃O)₂-C₆H₃- | CH₃ | O | 167–168 | Ethanol-dichloromethane | 89.1 |
| 31 | 0 | 2 | 2-Cl-C₆H₄- | CH₃ | O | 93–94 | Ether-hexane | 67.6 |
| 32 | 0 | 2 | 4-HO-C₆H₄- | CH₃ | O | 213–214 | Methanol-chloroform | 67.3 |

EXAMPLE 33

A mixture of 2-imino-5-[4-(5-methyl-2-phenyl-4-oxazolylmethoxy)benzyl]-4-thiazolidinone (11.4 g), 1N.H₂SO₄ (100 ml) and dioxane (100 ml) was stirred at 80° C. for 5 hours, and poured in water. The aqueous mixture was extracted with chloroform. The chloroform layer was washed with water, dried (MgSO₄) and concentrated. The oily residue was chromatographed on a column of silica gel (200 g), and from the fractions eluted with chlorform-methanol (100:1, V/V), there was obtained 5-[4-(5-methyl-2-phenyl-4-oxazolylmethoxy)benzyl]-2,4-thiazolidinedione (6.7 g, 58.8%). Recrystallization from ethyl acetate-hexane afforded colorless plates. m.p. 162°–163° C. Elemental analysis for C₂₁H₁₈N₂O₄S, Calcd.: C, 63.95; H, 4.60; N, 7.10. Found: C, 63.84; H, 4.63; N, 6.90. This product showed the IR and NMR spectra in accordance with those of the compound obtained in Example 6.

EXAMPLE 34

A mixture of 2-imino-5-<4-{2-[5-methyl-2-(1-methylcyclohexyl)-4-oxazolyl]ethoxy}benzyl>-4-thiazolodinone (9.5 g), 2N HCl (100 ml) and ethanol (100 ml) was heated under reflux for 15 hours. The reaction solution was poured into water, and the aqueous mixture was extracted with ethyl acetate. The ethyl acetate layer was washed with water, dried (MgSO₄) and concentrated. The oily residue was dissolved in methanol (10 ml), and 10 g of 28% solution of sodium methylate in methanol was added to the solution. Ether (100 ml) was added to the solution, and the crystals which separated out were collected by filtration and recrystallization from ethanol gave 5<4-{2-[5-methyl- 2-(1-methylcyclohexyl)-4-oxazolyl]ethoxy}benzyl>-2,4-thiazolidinedione.sodium salt (5.1 g, 51.5%). Colorless prisms, m.p. 250°-251° C. (decomp.). Elemental analysis for $C_{23}H_{27}N_2O_4SNa$, Calcd.: C, 61.32; H, 6.04; N, 6.22. Found: C, 61.47; H, 6.15; N, 6.48.

EXAMPLES 35 TO 37

By a procedure similar to that of Example 34, there were obtained the compounds shown in Table 3.

(2) The oily substance (about 8 g) obtained in (1) was dissolved in dioxane (100 ml), and 2N.HCl (100 ml) was added to the solution. The mixture was refluxed for 7 hours and poured into water. The aqueous mixture was extracted with ethyl acetate. The ethyl acetate layer was washed with water, dried (MgSO$_4$) and concentrated, and the residue was chromatographed on a column of silica gel (200 g). From the fractions eluted with ether-hexane (1:1, V/V), there was obtained 5-{4-[2-(5-hydroxymethyl-2-phenyl-4-oxazolyl)ethoxy]benzyl}-2,4-thiazolidinedione (1.31 g, 21.0%). Recrystallization from acetone-hexane yielded colorless scales. m.p. 98°-99° C. Elemental analysis for $C_{22}H_{20}N_2O_5S$, Calcd.: C, 62.25; H, 4.75; N, 6.60. Found: C, 62.08; H, 4.56; N, 6.49.

TABLE 3

[Structure: R¹-C(=N)-X-C(R²)=C-CH₂CH₂O-C₆H₄-CH₂-CH(-S-C(=O)-N.Na-)C=O]

| Example No. | R¹ | R² | X | Melting point °C. (decomp.) | Recrystallizing solvent | Yield % |
|---|---|---|---|---|---|---|
| 35 | cyclohexyl | H | S | 289–291 | Methanol | 81.0 |
| 36 | cyclohexyl | H | O | 269–271 (½ hydrate) | Ethanol | 33.6 |
| 37 | cyclohexyl | CH₃ | O | 273–275 | Methanol-ethanol | 71.2 |

EXAMPLE 38

(1) N-Bromosuccinimide (2.75 g) was added portionwise to a solution of 5-{4-[2-(5-methyl-2-phenyl-4-oxazolyl)ethoxy]benzyl}-2,4-thiazolidinedione (6.0 g) and α,α'-azobisisobutyronitrile (0.5 g) in carbon tetrachloride(150 ml) under reflux. After refluxing for another 10 minutes, the reaction mixture was washed with water and dried (MgSO$_4$). The solvent was distilled off to give 5-{4-[2-(5-bromomethyl-2-phenyl-4-oxazolyl)ethoxy]benzyl}-2,4-thiazolidinedione as a crude oily substance (about 8 g). IR (neat) cm$^{-1}$: 1750, 1690. NMRδ(ppm) in CDCl$_3$: 3.03 (2 HtJ=7 Hz), 2.9 to 3.2 (1H, m), 3.48 (1H, d.d, J=14 and 5 Hz), 4.24 (2H, t, J=7 Hz), 4.45 (1h, d.d, J=9 and 5 Hz), 4.61 (2H, s), 6.81 (2H, d, J=9 Hz), 7.10 (2H, d, J=9 Hz), 7.4 (3H, m), 8.0 (2H, m), 8.70 (1H, broad s).

EXAMPLE 39

By a procedure similar to that of Example 1, there was obtained 5-[4-(4-thiazolylmethoxy)benzyl]-2,4-thiazolidinedione. Yield of 18.1%. Recrystallization from acetone-hexane afforded colorless needles, m.p. 151°-153° C. Elemental analysis for $C_{14}H_{12}N_2O_3S_2$, Calcd.: C, 52.42; H, 3.78; N, 8.74. Found: C, 52.75; H, 3.78; N, 8.74.

EXAMPLES 40 TO 45

By a procedure similar to that of Example 12, there were obtained the compounds shown in Table 4.

[Structure: R¹-C(=N)-O-C(R²)=C-(CH(OH))$_m$-(CH$_2$)$_n$-O-C$_6$H$_4$-CH$_2$-CH(-S-C(=O)-NH-)C=O]

| Example No. | m | n | R¹ | R² | Melting point, °C. | Recrystallizing solvent | Yield % |
|---|---|---|---|---|---|---|---|
| 40 | 0 | 2 | cyclohexyl-CH₂ | CH₃ | 135–136 | Acetone-hexane | 89.4 |

-continued

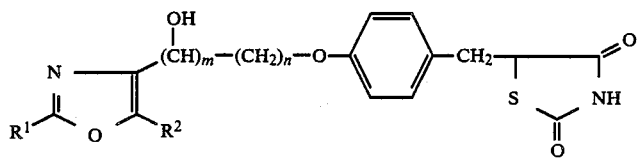

| Example No. | m | n | R¹ | R² | Melting point, °C. | Recrystallizing solvent | Yield % |
|---|---|---|---|---|---|---|---|
| 41 | 0 | 2 | 4-Cl-C₆H₄ | CH₃ | 173–174 | Ethanol | 92.1 |
| 42 | 0 | 2 | 3-CH₃S-C₆H₄ | CH₃ | 161–162 | Ethanol | 95.0 |
| 43 | 0 | 2 | 3-CF₃-C₆H₄ | CH₃ | 163–164 | Ethanol | 88.0 |
| 44 | 1 | 1 | cyclohexyl | CH₃ | Oily material | — | 55.0 |
| 45 | 0 | 3 | C₆H₅ | CH₃ | 130–131 | Ethyl acetate-hexane | 94.0 |

EXAMPLE 46

By a procedure similar to that of Example 34, there was obtained 5-<4-{2-[5-methyl-2-(1-methyl-3-cyclohexenyl)-4-oxazolyl]ethoxy}benzyl>-2,4-thiazolidinedione.sodium salt. Yield 79.2%. Recerystallization from methanol-ethyl acetate afforded colorless prisms. m.p. 245°–246° C. (decomp.). Elemental analysis for $C_{23}H_{25}N_2O_4SNa$, Calcd.: C, 61.59; H, 5.62; N, 6.25. Found: C, 61.70; H, 5,59; N, 6.01.

EXAMPLE 47

Acetic anhydride (1.0 ml) was added to a solution of 5-{4-[2-(2,5-dimethyl-4-oxazolyl)-2-hydroxyethoxy]-benzyl}-2,4-thiazolidinedione (0.5 g) in dimethylsulfoxide (10 ml), and the mixture was allowed to stand overnight and poured into water. The mixture was extracted with ethyl acetate. The ethyl acetate layer was washed with water, dried (MgSO₄) and concetrated. The oily residue was chromatographed on a column of silica gel (40 g), and from the fractions eluted with benzene-acetone (9:1 V/v), there was obtained 5-{4-[2-(2,5-dimethyl-4-oxazolyl)-2-oxoethoxy]benzyl}-2,4-thiazolidinedione (0.24 g, 48.3%). Recrystallization from ethyl acetate-hexane afforded colorless plates, m.p. 161°–162° C.

Elemental analysis for $C_{17}H_{16}N_2O_5S$, Calcd.: C, 56.66; H, 4.47; N, 7.77. Found: C, 56.62; H, 4.38; N, 7.60.

EXAMPLE 48

By a procedure similar to that of Example 47, there was obtained 5-{4-[2-(5-methyl-2-phenyl-4-oxazolyl)-2-oxoethoxy]benzyl}-2,4-thiazolidinedione. Yield 81.3% Recrystallization from ethyl acetate-hexane afforded colorless prisms, m.p. 168°–169° C.

EXAMPLE 49

A mixture of 4-[2-(5-methyl-2-phenyl-4-oxazolyl)ethoxy]benzaldehyde (5.0 g), 2,4-thiazolidinedione (3.8 g), piperidine (0.32 ml) and ethanol (100 ml) was stirred under reflux for 5 hours. After cooling, the crystals which separated out were collected by filtration to give 5-{4-[2-(5-methyl-2-phenyl-4-oxazolyl)ethoxy]benzylidene}-2,4-thiazolidinedione (5.1 g, 76.8%). Recrystallization from chloroform-ethanol afforded colorless needles, m.p. 213°–214° C. Elemental analysis for $C_{22}H_{18}N_2O_4S$, Calcd.: C, 65.01; H, 4.46; N, 6.89. Found: C, 64.81; H, 4.55; N, 6.78.

EXAMPLES 50 TO 63

By following a procedure similar to that of Example 48, there were obtained the compounds as shown in Table 5.

TABLE 5

[Structure: imidazole/thiazole ring with R¹-X, R² substituents, connected via (Y)ₘ—(CH₂)ₙ—O—phenyl—CH₂—thiazolidine-2,4-dione]

| Example No. | R¹ | R² | X | m | Y | n | Melting point, °C. | Recrystallizing solvent | Yield % |
|---|---|---|---|---|---|---|---|---|---|
| 50 | CH₃ | H | S | 0 | — | 2 | 215–216 | Ethanol-chloroform | 81.6 |
| 51 | phenyl | H | S | 0 | — | 1 | 235–237 | Methanol-chloroform | 89.9 |
| 52 | phenyl | H | S | 0 | — | 2 | 210–211 | Methanol-chloroform | 90.6 |
| 53 | phenyl | H | O | 0 | — | 1 | 244–246 | DMF-water | 80.5 |
| 54 | phenyl | C₂H₅ | O | 0 | — | 2 | 175–176 | Ethanol-chloroform | 71.9 |
| 55 | 2-chlorophenyl | CH₃ | O | 0 | — | 2 | 217–218 | Ethanol-chloroform | 82.7 |
| 56 | 4-chlorophenyl | CH₃ | O | 0 | — | 2 | 214–215 | Ethanol-dichloromethane | 91.2 |
| 57 | 4-(CH₃S)phenyl | CH₃ | O | 0 | — | 2 | 185–187 | Ethanol-chloroform | 67.0 |
| 58 | 3,4-dimethoxyphenyl | CH₃ | O | 0 | — | 2 | 243–244 | DMF-water | 83.1 |
| 59 | 2-thienyl | CH₃ | O | 0 | — | 2 | 221–222 | Ethanol-chloroform | 48.2 |
| 60 | CH₃ | CH₃ | O | 1 | —CO— | 1 | 234–235 | Ethanol-chloroform | 62.7 |
| 61 | phenyl | CH₃ | O | 1 | —CH(OH)— | 1 | 252–253.5 | Methanol-chloroform | 58.6 |

TABLE 5-continued

| Example No. | R¹ | R² | X | m | Y | n | Melting point, °C. | Recrystallizing solvent | Yield % |
|---|---|---|---|---|---|---|---|---|---|
| 62 | cyclohexyl-C(CH₃)(H)- | CH₃ | O | 0 | — | 2 | 172-175 | Ethanol-chloroform | 53.1 |
| 63 | cyclohexenyl-C(CH₃)- | CH₃ | O | 0 | — | 2 | 158-159 | Ethanol-chloroform | 56.0 |

EXAMPLE 64

60% sodium hydride in oil (0.24 g) was added to a solution of 5-(4-hydroxybenzylidene)-2,4-thiazolidinedione (0.664 g) in N,N-dimethylformamide (20 ml), and the mixture was stirred for 30 minutes. A solution of 4-chloromethyl-5-methyl-2-phenyloxazole (0.623 g) in N,N-dimethylformamide (10 ml) was added dropwise to the mixture under ice-cooling. After stirring at room temperature for 5 hours, the reaction solution was poured into water. The aqueous mixture was made acid with acetic acid and extracted with ethyl acetate. The ethyl acetate layer was washed with water, dried (MgSO₄) and concentrated. The residue was chromatographed on a column of silica gel (50 g). From the fractions eluted with ethyl acetatehexane (1:2, V/V), there was obtained 5-[4-(5-methyl-2-phenyl-4-oxazolylmethoxy)benzylidene]-2,4-thiazolidinedione (0.49 g, 40.8%). Recrystallization from chloroform-methanol afforded colorless prisms, m.p. 225°-226° C. Elemental analysis for $C_{21}H_{16}N_2O_4S$, Calcd.: C, 64.27; H, 4.11; N, 7.14. Found: C, 64.49; H, 3.96; H, 6.86.

EXAMPLE 65

60% sodium hydride in oil (0.24 g) was added to a solution of 5-(4-hydroxybenzylidene)-2,4-thiazolidinedione (0.663 g) in N,N-dimethylformamide (20 ml) and the mixture was stirred for 30 minutes. Then, a solution of 4-bromoacetyl-5-methyl-2-phenyloxazole (0.841 g) in N,N-dimethylformamide (10 ml) was added dropwise to the mixture under ice-cooling. After stirring under ice-cooling for 30 minutes, the reaction solution was poured into ice-cold water. The aqueous mixture was made acid with acetic acid. The solid which precipitated was collected by filtration, washed with water, and crystallized from acetone to give 5-{4-[2-(5-methyl-2-phenyl-4-oxazolyl)-2-oxoethoxy]benzylidene}-2,4-thiazolidinedione (0.42 g, 32.3%). Recrystallization from chloroform-ethanol yielded colorless needles, m.p. 244°-245° C. Elemental analysis for $C_{22}H_{16}N_2O_5S$, Calcd.: C, 62.85; H, 3.84; N, 6.66. Found: C, 62.80; H, 3.69; N, 6.93.

EXAMPLE 66

Sodium borohydride (0.16 g) was added to a suspension of 5-{4-[2-(2,5-dimethyl-oxazolyl)-2-oxoethoxy]benzylidene}-2,4-thiazolidinedione (1.5 g) in methanol-N,N-dimethylformamide (1:1, V.V, 40 ml) under ice-cooling. After stirring under ice-cooling for 20 minutes, the reaction solution was poured into ice-water, and the aqueous mixture was made acid with acetic acid, and the crystals which separated out were collected by filtration to give 5-{4-[2-(2,5-dimethyl-4-oxazolyl)-2-hydroxyethoxy]benzyl}-2,4-thiazolidinedione (1.47 g, 97.5%). Recrystallization from chloroform-ethanol afforded colorless prisms, m.p. 223°-224° C. Elemental analysis for $C_{17}H_{16}N_2O_5S$, Calcd.: C, 56.66; H, 4.47; N, 7.77. Found: C, 56.36; H, 4.55; N, 7.56.

EXAMPLE 67

By a procedure similar to that of Example 66, there was obtained 5-{4-[2-hydroxy-2-(5-methyl-2-phenyl-4-oxazolyl)ethoxy]benzylidene}-2,4-thiazolidinedione (the same compound as that obtained in Example 61 from 5-{4-[2-(5-methyl-2-phenyl-4-oxazolyl)-2-oxoethoxy]benzylidene}-2,4-thiazolidinedione. M.p. 252°-253° C. Yield 98.4%.

EXAMPLE 68

0.32 ml of 28% sodium methylate in methanol was added dropwise to a suspension of 5-{4-[2-(5-methyl-2-phenyl-4-oxazolyl)ethoxy]benzylidene}-2,4-thiazolidinedione (0.50 g) in methanol (10 ml). The reaction solution was concentrated, and diluted with ehyl ether. The crystals which separated out were collected by filtration to give sodium salt (0.43 g, 81.6%) of 5-{4-[2-(5-methyl-2-phenyl-4-oxazolyl)ethoxy]benzylidene}-2,4-thiazolidinedione. Recrystallization from methanol afforded colorless prisms, m.p. 286°-288° C. (decomp.). Elemental analysis for $C_{22}H_{17}N_2 \cdot O_4SNa$, Calcd.: C, 61.68; H, 4.00; N, 6.54. Found: C, 61.44; H, 3.82; N, 6.85.

EXAMPLE 69

A stirred mixture of 5-{4-[2-(5-methyl-2-phenyl-4-oxazolyl)ethoxy]benzylidene}-2,4-thiazolidinedione (500 mg), 10% Pd-C (50% wet, 1.0 g) and acetic acid (50 ml) was hydrogenated at 70° C. and at atmospheric pressure for 3 hours. Methanol (20 ml) and chloroform (20 ml) were added to the mixture and the whole was heated at 60° C. for 5 minutes. The mixture was filtered hot and the filtrate was concentrated in vacuo. A solution of the residue in ethyl acetate was successively washed with saturated aqueous sodium bicarbonate solution and water, and dried over magnesium sulfate.

The solvent was removed and the residue was recrystallized from ethanol to yield 5-{4-[2-(5-methyl-2-phenyl-4-oxazolyl)ethoxy]benzyl}-2,4-thiazolidinedione (the same compound as that obtained in Example 12) as crystals (415 mg, 82.7%). m.p. 113°–114° C.

EXAMPLE 70

A stirred mixture of 5-{4-[2-(5-methyl-2-phenyl-4-oxazolyl)-2-oxoethoxy]benzylidene}-2,4-thiazolidinedione (1.0 g), Pd-black (3 g) and dioxane (100 ml) was hydrogenated at 40° C. and at atmospheric pressure. After 4 hours, another Pd-black (3 g) was added and hydrogenation was continued for 4 hours. The catalyst was filtered off and the filtrate was concentrated to yield 5-{4-[2-(5-methyl-2-phenyl-4-oxazolyl)-2-oxoethoxy]benzyl}-2,4-thiazolidinedione (the same compound as that obtained in Example 48) as crystals (0.95 g, 94.1%). Recrystallization from ethyl acetate-hexane gave colorless needles, m.p. 168°–169° C.

REFERENCE EXAMPLE 1

A mixture of butyramide (19.88 g) and 1.3-dichloroacetone (24.14 g) was heated at 130° C. for 1.5 hours. After cooling, the mixture was diluted with water, neutralized with aqueous sodium bicarbonate solution and extracted with ethyl ether. The extract was washed with water, dried (MgSO$_4$) and concentrated. The residue was purified by chromatography on silica gel with acetone-hexane (1:9) to yield 4-chloromethyl-2-propyloxazole as an oil (10.70 g 35.3%). NMR (CDCl$_3$)δ: 0.97 (3H, t, J=7.5 Hz), 1.79 (2H, sext, J=7.5 Hz), 2.72 (2H, t, J=7.5 Hz), 4.47 (2H, s), 7.53 (1H, s).

REFERENCE EXAMPLE 2

A mixture of benzamide (60.0 g) and ethyl 4-chloroacetoacetate (49.4 g) was heated at 120° C. for 2 hours. After cooling, aqueous sodium bicarbonate solution was added thereto and the mixture was extracted with ethyl acetate. The extract was washed with water, dried (MgSO$_4$) and concentrated. The residue was purified by chromatography on silica gel with ethyl ether-hexane (1:9) to yield ethyl 2-phenyl-4-oxazoleacetate as an oil (26.4 g, 28.0%). NMR (CDCl$_3$)δ: 1.27 (3H, t, J=7 Hz), 3.68 (3H, s), 4.15 (2H, q, J=7 Hz), 7.4 (3H, m), 7.67 (1H, s), 8.0 (2H, m).

REFERENCE EXAMPLE 3

A mixture of cyclohexanethiocarboxamide (5.0 g), ethyl 4-chloroacetoacetate (5.74 g), ethanol (50 ml) was heated under reflux for 1 hour. After dilution with water, mixture was extracted with ethyl acetate. The extract was washed with aqueous sodium bicarbonate solution and water, dried (MgSO$_4$), and concentrated. The residue was purified by chromatography on silica gel with ethyl acetate-hexane (1:4) to yield ethyl 2-cyclohexyl-4-thiazoleacetate as an oil (6.3 g, 70.9%). IR (Neat): 1735, 1255 cm$^{-1}$. NMR (CDCl$_3$)δ: 1.28 (3H, t, J=7 Hz), 1.2–2.3 (10H, m), 2.97 (1H, m), 3.77 (2H, s), 4.17 (2H, q, J=7 Hz), 7.0 (1H, s).

REFERENCE EXAMPLE 4

A solution of methyl 5-methyl-2-phenyl-4-oxazoleacetate (54 g) in dry ethyl ether (150 ml) was added dropwise to a stirred, ice-cooled suspension of lithium aluminum hydride (8.8 g) in dry ethyl ether (700 ml) during 1.5 hours. Ethyl acetate (20 ml) was added dropwise thereto with ice-cooling and then water (50 ml) was added cautiously thereto. The resulting white precipitate was filtered off and the filtrate was concentrated to give 2-(5-methyl-2-phenyl-4-oxazolyl) ethanol as crystals (45.8 g, 96.2%). Recrystallization from ethyl acetate-hexane gave colorless rods, m.p. 73°–74° C.

REFERENCE EXAMPLE 5

2-(2,5-Dimethyl-4-oxazolyl)ethanol (17.0 g) and 4-fluoronitrobenzene (17.0 g) were dissolved in N,N-dimethylformamide (150 ml), and 60% sodium hydride in oil (6.0 g) was added dropwise to the solution under vigorous stirring. After stirring at room temperature for 1 hour, the reaction mixture was poured into water (1 l) and the crystals which separated out were collected by filtration and recrystallized from ethyl acetate-hexane to give 4-[2-(2,5-dimethyl-4-oxazolyl)ethoxy]nitrobenzene (27.5 g. 87.0%). Colorless columns, m.p. 97°–98° C. Elemental analysis for C$_{13}$H$_{14}$N$_2$O$_4$, Calcd.: C, 59.94; H, 5.38; N, 10.68. Found: C, 59.72; H, 5.44; N, 10.63.

By a procedure similar to the above procedure, there were obtained the compounds shown in Table 6.

TABLE 6

![structure]

| R$^1$ | R$^2$ | X | Melting point, °C. | Recrystallizing solvent | Yield % |
| --- | --- | --- | --- | --- | --- |
| CH$_3$ | H | S | 101–102 | Methanol-ether | 70.0 |
| CH$_3$ | H | O | 101–102 | Methanol | 71.3 |
| 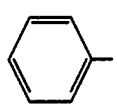 | H | S | 102–103 | Methanol | 50.2 |
| 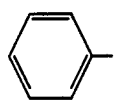 | H | O | 112–113 | Methanol | 92.2 |

TABLE 6-continued
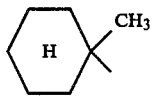
| R¹ | R² | X | Melting point, °C. | Recrystallizing solvent | Yield % |
|---|---|---|---|---|---|
|  | CH₃ | O | Oily material | — | 92.0 |
|  | CH₃ | O | 94–95 | Methanol | 80.1 |
| C₃H₇ | H | O | 70–71 | Ether-hexane | 47.6 |
| 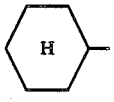 | H | S | 62–63 | Methanol | 73.2 |
| 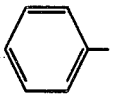 | H | O | 61–62 | Methanol | 70.6 |
| C₂H₅ | H | S | 63–64 | Ethyl acetate-hexane | 75.7 |
| i-C₃H₇ | H | S | 62–63 | Ethyl acetate-hexane | 67.8 |
| 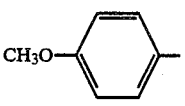 | C₂H₅ | O | 71–72 | Ethanol | 91.6 |
| 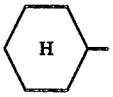 | CH₃ | O | 113–114 | Ethyl acetate-hexane | 82.1 |
| CH₃ | C₂H₅ | O | 89–90 | Ether-hexane | 77.6 |
| 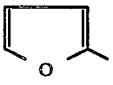 | CH₃ | O | Oily material | — | 70.5 |
| 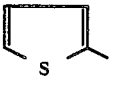 | CH₃ | O | 121–122 | Methanol-dichloromethane | 69.1 |
| 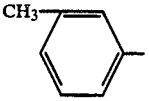 | CH₃ | O | 107–108 | Methanol-water | 74.7 |
|  | CH₃ | O | 79–80 | Ethanol | 85.4 |

TABLE 6-continued

Structure:

R¹—C(=N)—X—C(R²)=C(CH₂CH₂O—C₆H₄—NO₂)— (oxazole/thiazole ring)

| R¹ | R² | X | Melting point, °C. | Recrystallizing solvent | Yield % |
|---|---|---|---|---|---|
| 3,4-(CH₃O)₂-C₆H₃- | CH₃ | O | 124–125 | Ethanol-chloroform | 91.5 |
| 2-Cl-C₆H₄- | CH₃ | O | 89–90 | Ether-hexane | 58.0 |
| C₆H₅-CH₂O-C₆H₄- | CH₃ | O | 137–138 | Methanol-dichloromethane | 74.2 |

REFERENCE EXAMPLE 6

(1) A solution of 4-[2-(5-methyl-2-phenyl-4-oxazolyl)ethoxy]nitrobenzene (10.5 g) in methanol (100 ml) was subjected to a catalytic hydrogenation over 10% Pd-C (50% wet, 3.0 g). After the catalyst was filtered off, the filtrate was concentrated to give an amino derivative as an oily substance. This amino derivative was dissolved in acetone (100 ml)-methanol (100 ml), followed by addition of a 47% aqueous HBr solution (22 g). A solution of NaNO₂ (2.4 g) in water (8 ml) was added dropwise to the solution at a temperature of not higher than 5° C. After the solution was stirred at 5° C. for 15 minutes, methyl acrylate (16.3 g) was added, and the reaction mixture was warmed to 38° C. Powdered cuprous oxide (1 g) was added in small portions to the mixture with vigorous stirring. After stirring was continued until evolution of nitrogen gas stopped, the reaction mixture was concentrated. The residue was made basic with aqueous ammonia, and the aqueous mixture was extracted with ethyl acetate. The ethyl acetate layer was washed with water, dried (MgSO₄) and concentrated to give methyl 2-bromo-3-{4-[2-(5-methyl-2-phenyl-4-oxazolyl)ethoxy]phenyl}propionate as a crude oily material (12.6 g, 88.7%).

IR (neat) cm⁻¹: 1735. NMRδ(ppm) in CDCl₃: 2.33 (3H, s), 2.93 (2H, t, J=7 Hz), 3.0 to 3.5 (2H, m), 3.65 (3H, s), 4.0 to 4.4 (3H, m), 6.6 to 7.2 (4H, m), 7.4 (3H, m), 7.9 (2H, m).

(2) Thiourea (2.1 g) and sodium acetate (2.3 g) were added to a solution of the oily material (12.4 g) as obtained in (1) in ethanol (100 ml), and the mixture was stirred under reflux for 3 hours. The reaction mixture was concentrated, and the residue was neutralized with aqueous saturated sodium bicarbonate solution, followed by addition of ether (50 ml)-hexane (50 ml). After stirring for 10 minutes, the crystals which separated out were collected by filtration to give 2-imino-5-{4-[2-(5-methyl-2-phenyl-4-oxazlyl)ethoxy]benzyl}-4-thiazolidinone (6.1 g, 53.5%). Recrystallization from ethanol afforded colorless prisms, m.p. 212°–213° C. Elemental analysis for C₂₂H₂₁N₃O₃S; Calcd.: C, 64.85; H, 5.19; N, 10.31. Found: C, 64.85; H, 5.00; N, 10.25.

By a procedure similar to the above-described one, there were obtained the compounds as shown in Table 7. The yield is expressed in terms of an over-all yield based on the starting nitro derivative.

TABLE 7

Structure: R¹—C(=N)—X—C(R²)=C—CH₂CH₂O—C₆H₄—CH₂—CH(—S—C(=NH)—NH—C(=O)—)

| R¹ | R² | X | Melting point, °C. | Recrystallizing solvent | Yield % |
|---|---|---|---|---|---|
| CH₃ | H | S | 185–186 | Methanol | 28.4 |
| CH₃ | H | O | 202–204 | Methanol-dichloromethane | 46.6 |
| C₆H₅- | H | S | 182–183 | Methanol | 44.9 |

TABLE 7-continued

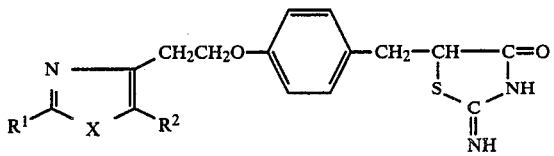

| R¹ | R² | X | Melting point, °C. | Recrystallizing solvent | Yield % |
|---|---|---|---|---|---|
| phenyl | H | O | 211–213 | Methanol-dichloromethane | 42.3 |
| $CH_3$ | $CH_3$ | O | 239–240 | Methanol-dichloromethane | 56.0 |
| 1-methylcyclohexyl | $CH_3$ | O | 180–181 | Ethanol | 51.6 |
| $C_3H_7$ | H | O | 175–176 | Methanol | 38.3 |
| cyclohexyl | H | S | 182–184 | Methanol | 32.1 |
| cyclohexyl | H | O | 203–205 | Methanol-dichloromethane | 38.4 |
| $C_2H_5$ | H | S | 168–169 | Methanol | 46.9 |
| $i$-$C_3H_7$ | H | S | 172–173 | Methanol-dichloromethane | 42.5 |
| phenyl | $C_2H_5$ | O | 190–191 | Ethanol | 23.7 |
| 4-methoxyphenyl | $CH_3$ | O | 213–214 | Ethanol | 53.5 |
| $CH_3$ | $C_2H_5$ | O | 208–209 | Ethanol-chloroform | 33.8 |
| cyclohexyl | $CH_3$ | O | 171–172 | Ethanol-water | 38.8 |
| 2-furyl | $CH_3$ | O | 222–224 | Methanol-dichloromethane | 41.0 |
| 3-methylphenyl | $CH_3$ | O | 194–195 | Ethanol | 45.0 |
| 3,4-dimethoxyphenyl | $CH_3$ | O | 197–198 | Ethanol-chloroform | 32.6 |

REFERENCE EXAMPLE 7

To a stirred solution of 4-acetyl-5-methyl-2-phenyloxazole (12.0 g) in chloroform (100 ml) was added at 50° C. a solution of bromine (10.5 g) in chloroform (10 ml). The mixture was further heated at 55° C. for 30 minutes and poured into saturated aqueous sodium bicarbonate solution (500 ml). The chloroform layer was separated and the aqueous layer was extracted with chloroform. The conbined chloroform layer was washed with water and dried (MgSO$_4$). Evaporation of the solvent gave 4-bromoacetyl-5-methyl-2-phenyloxazole as crystals (14.5 g, 86.3%). Recrystallization from ethyl ether-hexane gave colorless rods, mp 88°–89° C.

REFERENCE EXAMPLE 8

(1) A mixture of 4-bromoacetyl-5-methyl-2-phenyloxazole (33.8 g), p-hydroxyacetanilide, potassium carbonate (27.6 g) and methyl ethyl ketone (400 ml) was stirred under reflux for 3 hours. The solvent was distilled off and 300 ml of water and ether (300 ml)-hexane (100 ml) were added to the residue. The mixture was stirred at room temperature for 10 minutes, and there were recovered by filtration the crystals (23.5 g, 58.3%) of 4-(4-acetamidophenoxyacetyl)-5-methyl-2-phenyloxazole which separated out. Recrystallization from ethanol afforded colorless prisms, m.p. 175°–176° C. Elemental analysis for $C_{20}H_{18}N_2O_4$; Calcd.: C, 68.56; H, 5.18; N, 8.00. Found: C, 68.53; H, 5.15; N, 8.05.

(2) 4-(4-acetamidophenoxyacetyl)-5-methyl-2-phenyloxazole (7.5 g) obtained in 1) was suspended in methanol (80 ml), and sodium borohydride (810 mg) was added portionwise to the suspension under ice-cooling. The mixture was stirred for 30 minutes. After acetic acid (2 ml) was added, the solution was poured into water, and the aqueous mixture was extracted with ethyl acetate. The ethyl acetate layer was washed with water, dried (MgSO$_4$) and concentrated to give 4-[2-hydroxy-2-(5-methyl-2-phenyl-4-oxazolyl)ethoxy]acetanilidie (6.8 g, 90.7%). Recrystallization from ethyl acetate afforded colorless needles, m.p. 166°–167° C. Elemental analysis for $C_{20}H_{20}N_2O_4S$; Calcd.: C, 68.17; H, 5.72; N, 7.95. Found: C, 68.26; H, 5.65; N, 8.11.

(3) A mixture of 4-[2-hydroxy-2-(5-methyl-2-phenyl-4-oxazolyl)ethoxy]acetanilide (11.5 g), 4N-KOH (100 ml) and ethanol (100 ml) was heated under reflux for 24 hours. The reaction solution was poured into water, and the crystals which separated out were collected by filtration and recrystallized from ethanol to give 4-[2-hydroxy-2-(5-methyl-2-phenyl-4-oxazolyl)ethoxy]aniline (9.7 g, 96.0%) as colorless prisms, m.p. 139°–140° C. Elemental analysis for $C_{18}N_{18}N_2O_3$; Calcd.: C, 69.66; H, 5.85; N, 9.03. Found: C, 69.43; H, 5.76; N, 8.95.

(4) 4-[2-Hydroxy-2-(5-methyl-2-phenyl-4-oxazolyl)ethoxy]aniline (18.5 g) was dissolved in methanol (50 ml)-acetone (150 ml), and 47% aqueous HBr (41.0 g) was added to the solution. Then, a solution of NaNO$_2$ (4.5 g) in water (10 ml) was added dropwise to the mixture at a temperature of not higher than 5° C. The whole was stirred at 5° C. for 15 minutes, and methyl acrylate (30.4 g) was added to the mixed solution, followed by warming at 38° C. Cuprous oxide (2.0 g) was added in small portions to the reaction solution with vigorous stirring, and stirring was continued until evolution of nitrogen gas stopped. After concentration, the residue was made basic with aqueous ammonia, and extracted with ethyl acetate. The ethyl acetate layer was washed with water, dried (MgSO$_4$) concentrated to give methyl 2-bromo-3-{4-[2-hydroxy-2-(5-methyl-2-phenyl-4-oxazolyl)ethoxy]phenyl}propionate as a crude oily material (27.0 g, 98.5%). IR (Neat) cm$^{-1}$: 3300, 1735. NMR δ (ppm) in CDCl$_3$: 2.40(3H, s), 3.0(1H, broad), 3.11(1H, d,d, J=14 and 7 Hz), 3.39(1H, d,d, J=14 and 7 Hz), 3.68(3H, s), 4.0 to 4.5(3H, m), 5.05(1H, d,d, J=8 and 5 Hz), 6.0 to 7.2(4H, m), 7.4 (3H, m), 7.9(2H, m).

(5) The oily material (27.0 g) obtained in 4) was dissolved in ethanol (270 ml), and thiourea (4.5 g) and sodium acetate (48 g) were added to the solution. The mixture was stirred under reflux for 4 hours and concentrated. The residue was neutralized with aqueous saturated sodium bicarbonate solution. Water (300 ml)-ether (200 ml) was aded to the mixture, followed by stirring at room temperature for 30 minutes. The crystals which separated out were collected by filtration to give 2-imino-5-{4-[2-hydroxy-2-(5-methyl-2-phenyl-4-oxazolyl)ethoxy]benzyl}-4-thiazolidinone (13.5 g, 54.0%). Recrystallization from methanol-chloroform afforded colorless needles, m.p. 238°–239° C. Elemental analysis for $C_{22}H_{21}N_3O_4S$; Calcd.: C, 62.40; H, 5.00; N, 9.92. Found: C, 62.24; H, 4.77; N, 9.79.

REFERENCE EXAMPLE 9

By a procedure similar to that of Reference Example 8, there were obtained the following compounds.

(1) 4-(4-Acetamidophenoxyacetyl)-2,5-dimethyloxazole: m.p. 223°–224° C. Yield 55.9%.

(2) 4-[2-(2,5-Dimethyl-4-oxazolyl)-2-hydroxyethoxy]acetanilide: m.p. 157°–158° C. Yield 93.3%.

(3) 4-[2-(2,5-Dimethyl-4-oxazolyl)-2-hydroxyethoxy]aniline: Oily material. IR (Neat) cm$^{-1}$: 3300(broad). Yield 99.1%.

(4) 2-Imino-5-{4-[2-hydroxy-2,5-dimethyl-4-oxazolyl)ethoxy]benzyl}-4-thiazolidinone: m.p. 238°–239° C. Yield 54.0%.

REFERENCE EXAMPLE 10

(1) A mixture of 4-chloromethyl-5-methyl-2-phenyloxazole (12.0 g), p-hydroxyacetanilide (13.1 g), potassium carbonate (16.6 g) and DMF (150 ml) was stirred at 110° C. for 3 hours and poured into water. The aqueous mixture was extracted with ethyl acetate and the ethyl acetate layer was washed with water, dried (MgSO$_4$) and concentrated to five 4-(5-methyl-2-phenyl-4-oxazolylmethoxy)acetanilide (18.0 g, 95.7%). Recrystallization from ethanol afforded colorless plates, m.p. 154°–155° C. Elemental analysis for $C_{19}H_{18}N_2O_3$: Calcd.: C, 70.79; H, 5.63; N, 8.69. Found: C, 70.67; H, 5.57; N, 8.58.

(2) A mixture of 4-(5-methyl-2-phenyl-4-oxazolylmethoxy)acetanilide (17.5 g) obtained in 1), 4H.KOH (150 ml) and ethanol (150 ml) was heated under reflux for 20 hours, and concentrated to about ⅓ of the original volume. The crystals which separated out were collected by filtration to give 4-(5-methyl-2-phenyl-4-oxazolylmethoxy)anilide 14.7 g, 96.7%). Recrystallization from ethanol afforded colorless prisms, m.p. 129°–130° C. Elemental analysis for $C_{17}H_{16}N_2O_2$; Calcd.: C, 72.84; H, 5.75; N, 9.99. Found: C, 72.79; H, 5.70; N, 9.87.

(3) 4-(5-methyl-2-phenyl-4-oxazolylmethoxy)aniline (14.5 g) obtained in 2) was subjected to reactions similar to those in Reference Example 8-4) and 5) to give 2-imino-5-[4-(5-methyl-2-phenyl-4-oxazolylmethoxy)benzyl]-4-thiazolidinone (11.8 g, 57.3%). Recrystallization from chloroform-methanol afforded colorless plates, m.p. 257°–258° C. Elemental analysis for $C_{21}H_{19}N_3O_3S$; Calcd.: C, 64.11; H, 4.87; N, 10.68. Found: C, 64.16; H, 4.80; N, 10.80.

REFERENCE EXAMPLE 11

(1) Reduced iron (10.6 g) was added portionwise mixture of 4-{2-[2-(2-chlorophenyl)-5-methyl-4-oxazolyl]ethoxy}nitrobenzene (22.9 g), acetic acid (150 ml) and water (50 ml) at 70° C. After stirring at 80° C. for 2 hours, the insoluble matter was filtered off, and the filtrate was concentrated under reduced pressure. Water was added to the filtrate, and the aqueous mixture was extracted with ethyl acetate. The ethyl acetate layer was washed with water, dried ($MgSO_4$) and concentrated to give 4-{2-[2-(2-chlorophenyl)-5-methyl-4-oxazolyl]ethoxy}aniline as a crude oily material (20.5 g, 97.6%). NMR δppm in $CDCl_3$: 2.35(3H, s), 2.93(2H, t, J=7 Hz), 3.77(2H, s), 4.15(2H, t, J=7 Hz), 6.56(2H, d, J=9 Hz), 6.75(2H, d, J=9 Hz), 7.2 to 7.5(3H, m), 7.9 (1H, m).

(2) The oily material (20.5 g) obtained in 1) was dissolved in acetone (100 ml)-methanol (100 ml), and 47% aqueous HBr (45 g) was added to the solution. Then, a solution of $NaNO_2$ (4.8 g) in water (10 ml) was added dropwise thereto at a temperature of not higher than 5° C. After stirring at 5° C. for 15 minutes, methyl acrylate (33 g) was added to the mixture and the whole was warmed to 38° C. Cuporous oxide (2 g) was added in small portions to the mixture with vigorous stirring, and stirring was continued until evolution of nitrogen gas stopped. The reaction solution was concentrated under reduced pressure and the residue was made basic with aqueous ammonia, and extracted with ethyl acetate. The ethyl acetate layer was washed with water, dried ($MgSO_4$) and concentrated to give methyl 2-bromo-3-<4-{2-[2-(2-chlorophenyl)-5-methyl-4-oxazolyl]ethoxy}phenyl>-propionate as a crude oily material (24.5 g). NMR (ppm) in $CDCl_3$: 2.37(3H, s), 2.97(2H, t, J=7 Hz), 3.12(1H, d.d, J=14 and 7 Hz), 3.38(1H, d.d, J=14 and 7 Hz), 4.1 to 4.4(3H, m), 6.7 to 7.5 (7H, m), 7.9(1H, m).

(3) The oily material (24.5 g) obtained in 2) was dissolved in ethanol (250 ml), and thiourea (4.9 g) and sodium acetate (5.2 g) were added to the solution. The mixture was heated under reflux for 10 hours, and concentrated. Water was poured onto the residue, and the crystals which separated out were collected by filtration. Recrystallization from ethanol-dichloromethane gave 5-<4-{2-(2-chlorophenyl)-5-methyl-4-oxazolyl]ethoxy}benzyl>-2-imino-4-thiazolidinone (9.6 g, 34.1%), m.p. 174°–176° C. Elemental analysis for $C_{22}H_{20}N_3O_3SCl$; Calcd.: C, 59.79; H, 4.56; N, 9.51. Found: C, 59.69; H, 4.60; N, 9.34.

REFERENCE EXAMPLE 12

By a procedure similar to that of Reference Example 11, there was obtained crystals (yield; 53.1% based on the corresponding nitro derivative) of 2-imino-5-<4-{2-[5-methyl-2-(2-thienyl)-4-oxazolyl]ethoxy}benzyl>-4-thiazolidinone. Recrystallization from methanol-dichloromethane afforded colorless prisms, m.p. 171°–172° C. Elemental analysis for $C_{20}H_{19}N_3O_3S_2$; Calcd.: C, 58.09; H, 4.63; N, 10.16. Found: C, 57.86; H, 4.59; N, 10.04.

REFERENCE EXAMPLE 13

(1) A solution of 4-{2-[2-(4-benzyloxyphenyl)-5-methyl-4-oxazolyl]ethoxy}nitrobenzene (10.65 g) in methanol (200 ml) was subjected to a catalytic hydrogenation over 10% Pd-C (50% wet, 4.0 g). After the catalyst was filtered off, the filtrate was concentrated to give 4-{2-[2-(4-hydroxyphenyl)-5-methyl-4-oxazolyl]ethoxy}aniline (6.21 g, 78.2%). Recrystallization from methanol afforded brownish prisms, m.p. 184°–185° C. Elemental analysis for $C_{18}H_{18}N_2O_3$; Calcd.: C, 69.66; H, 5.85; N, 9.03. Found: C, 69.69; H, 5.87; N, 9.01.

(2) The crystals (6.11 g) obtained in 1) were dissolved in acetone (40 ml)-methanol (20 ml), and 47% aqueous HBr (7.7 ml) was added to the solution. Then, a solution of $NaNO_2$ (1.44 g) in water (3 ml) was added dropwise to the mixture at a temperature of not higher than 5° C. After stirring at 5° C. for 15 minutes, methyl acrylate (12 ml) was added to the mixed solution, and the whole was warmed to 38° C. Powdered cuprous oxide (1 g) was added in small portions to the mixture with vigorous stirring. After stirring was continued until evolution of nitrogen gas stopped, the reaction mixture was concentrated. The residue was made basic with aqueous ammonia and extracted with ethyl acetate. The ethyl acetate layer was washed with water, dried ($MgSO_4$) and concentrared to give crude crystals of methyl 2-bromo-3-<4-{2-[2-(4-hydroxyphenyl)-5-methyl-4-oxazolyl]ethoxy}phenyl>propionate.

(3) The whole amount of the crystals obtained in (2) was dissolved in ethanol (100 ml), and thiourea (2.28 g) and sodium acetate (2.46 g) were added to the soltuion. The mixture was stirred under reflux for 2 hours. The reaction mixture was poured into water, and the crystals which separated out were collected by filtration and washed with water and ether successively. Recrystallization from methanol and dichloromethane yielded 2-imino-5-<4-{2-[2-(4-hydroxyphenyl)-5-methyl-4-oxazolyl]ethoxy}benzyl>-4-thiazolidinone (5.35 g, 66.5%), colorless prisms, m.p. 175°–177° C. Elemental analysis for $C_{22}H_{21}N_3O_4S \cdot \frac{1}{2}H_2O$; Calcd: C, 61.10; H, 5.13; N, 9.72. Found: C, 61.02; H, 4.92; N, 9.56.

REFERENCE EXAMPLE 14

By a procedure similar to that of Reference Example 5, there were obtained the compounds shown in Table 8.

TABLE 8 structure: $R^1$-C(=N)-O-C($R^2$)=C-$(CH_2)_n$-O-C$_6$H$_4$-$NO_2$

| n | $R^1$ | $R^2$ | Melting point, °C. | Recrystallizing solvent | Yield % |
|---|---|---|---|---|---|
| 2 | cyclohexyl-CH$_2$- (H) | CH$_3$ | Oily material | — | 80.3 |
| 2 | 1-methylcyclohexenyl (CH$_3$) | CH$_3$ | Oily material | — | 80.8 |
| 2 | 4-Cl-C$_6$H$_4$- | CH$_3$ | 153–154 | Ethyl acetate | 94.7 |

TABLE 8-continued

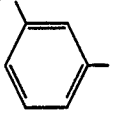

| n | R¹ | R² | Melting point, °C. | Recrystal- lizing solvent | Yield % |
|---|---|---|---|---|---|
| 2 | CH₃S-⌬- | CH₃ | 104-105 | Methanol | 87.5 |
| 2 | CF₃-⌬- | CH₃ | 112-113 | Ethyl acetate-hexane | 92.4 |
| 3 | ⌬- | CH₃ | 111-112 | Ethyl acetate-hexane | 90.0 |

REFERENCE EXAMPLE 15

By a procedure similar to that of Reference Example 6, there were obtained the compounds shown in Table 9. (The yield is expressed in terms of an over-all yield based on the starting nitro derivative).

TABLE 9

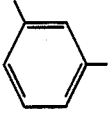

| n | R¹ | R² | Melting point, °C. | Recrystal- lizing solvent | Yield % |
|---|---|---|---|---|---|
| 2 | H-⌬-CH₂- | CH₃ | 180-182 | Methanol | 41.7 |
| 2 | ⌬<CH₃ | CH₃ | 136-138 | Ethyl acetate | 37.3 |
| 3 | ⌬- | CH₃ | 179-180 | Ethanol | 36.1 |

REFERENCE EXAMPLE 16

By a procedure similar to that of Refrence Example 8, there were obtained the following compounds.

(1) 4-(4-Acetamidophenoxyacetyl)-2-cyclohexyl-5-methyloxazole: m.p. 158°-159° C. Yield 48.1%.

(2) 4-[2-(2-Cyclohexyl-5-methyl-4-oxazolyl)-2-hydroxyethoxy]acetanilide: m.p. 125°-126° C. Yield 98.4%.

(3) 4-[2-(2-Cyclohexyl-5-methyl-4-oxazolyl)-2-hydroxyethoxy]aniline: Oily material. IR (neat) cm⁻¹: 3350 (broad). Yield 98.1%

(4) 5-{4-[2-(2-Cyclohexyl-5-methyl-4-oxazolyl)-2-hydroxyethoxy]benzyl}-2-imino-4-thiazolidinone: m.p. 167°-168° C. Yield of 34.4%.

REFERENCE EXAMPLE 17

By a procedure similar to that of Reference Example 11, there were obtained the following compounds.

(1) 4-{2-[2-(4-Chlorophenyl)-5-methyl-4-oxazolyl]ethoxy}aniline: m.p. 145°-146° C. Yield 59.9%.

(2) Methyl 2-bromo-3-<4-{2-[2-(4-chlorophenyl)-5-methyl-4-oxazolyl]ethoxy}phenyl>propionate: Oily material. IR (Neat) cm⁻¹: 1740. Yield 92.7%.

(3) 5-<4-{2-[2-(4-Chlorophenyl)-5-methyl-4-oxazolyl]ethoxy}benzyl<-2-imino-4-thiazolidinone: m.p. 238°-239° C. Yield 49.5%.

REFERENCE EXAMPLE 18

(1) A solution of 4-{2-[5-methyl-2-(3-methylthiophenyl)-4-oxazolyl]ethoxy}nitrobenzene (8.8 g) in methanol (100 ml) was subjected to catalytic hydrogenation over 10% Pd-C (50% wet, 10 g), and the catalyst was filtered off to give 4-{2-[5-methyl-2-(3-methylthiophenyl)-4-oxazolyl]ethoxy}aniline (5.9 g, 72.8%). Recrstallization from ethyl acetate-hexane afforded colorless prisms, m.p. 110°-111° C. Elemental analysis for $C_{19}H_{20}N_2O_2S$; Calcd.: C, 67.03; H, 5.92; N, 8.23. Found: C, 67.20; H, 5.94; N, 8.12.

(2) The crystals obtained in (1) was subjected to reactions similar to those in Refrence Example 13-(2) and (3) to give 2-imino-5-<4-{2-[5-methyl-2-(3-methylthiophenyl)-4-oxazolyl]ethoxy}benzyl>-4-thiazolidinone. Recrystallization from ethyl acetate-methanol afforded colorless prisms, m.p. 182°-183° C. Elemental analysis for $C_{23}H_{23}N_3O_3S_2$; Calcd.: C, 60.91; H, 5.11; N, 9.26. Found: C, 60.42; H, 4.76; N, 9.06.

REFERENCE EXAMPLE 19

By a procedure similar to that of Reference Example 18, there were obtained the following compounds.

(1) 4-{2-[5-methyl-2-(3-trifluoromethylphenyl)-4-oxazolyl]ethoxy}aniline: m.p. 121°-122° C. Yield 97.5%.

(2) 2-Imino-5-<4-{2-[5-methyl-2-(3-trifluoromethylphenyl)-4-oxazolyl]ethoxy}benzyl>-4-thiazolidinone. m.p. 212°-213° C. Yield 42.2%.

REFERENCE EXAMPLE 20

A solution of (Z)-5-{4-[2-(5-methyl-2-phenyl-4-oxazolyl)ethoxy]benzylidene}-2,4-thiazolidinedione (200 mg) in acetonitrile (750 ml), in a quartz tube under a stream of nitrogen, was irradiated by a 300 W high-pressure mercury lamp for 3 hours. The solvent was distilled off, and the resulting crystals were chromatographed on a column of silica gel (200 g). Elution with hexane-ethyl acetate (1:1, V/V) gave (E)-5-{4-[2-(5-methyl-2-phenyl-4-oxazolyl)ethoxy]benzylidene}-2,4-thiazolidinedione (40 mg, 20.0%). Recrystallization from dichloromethaneethanol yielded colorless needles, m.p. 216°-217° C. Elemental analysis for $C_{22}H_{18}N_2O_4S$; Calcd.: C, 65.01; H, 4.46; N, 6.89. Found: C, 64.69; H, 4.26; N, 7.11. The subsequent elution with hexane-ethyl acetate (1:1, V/v) allowed the recovery of (Z)-5-{4-[2-

(5-methyl-2-phenyl-4-oxazolyl)ethoxy]benzylidene}-2,4-thiazolidinedione (138 mg, 69.0%).

REFERENCE EXAMPLE 21

2-(5-Methyl-2-phenyl-4-oxazolyl)ethanol (6.0 g) and 4-fluorobenzonitrile (5.4 g) were dissolved in tetrahydrofurane (70 ml ), and 60% sodium hydride in oil (1.4 g) was added to the solution under ice-cooling with vigorous stirring. The reaction mixture was stirred at room temperature for 18 hours and poured into ice-cold water (0.5 l). The aqueous mixture was neutralized with acetic acid, and the crystals which separated out were collected by filtration to give 4-[2-(5-methyl-2-phenyl-4-oxazolyl)ethoxy]benzonitrile (7.0 g, 77.5%). Recrystallization from ether-hexane afforded colorless prisms, m.p. 119°–120° C. Elemental analysis for $C_{19}H_{16}N_2O_2$; Calcd: C, 74.98; H, 5.30; N, 9.20. Found: C, 74.90; H, 5.01; N, 9.28.

By a procedure similar to the above, there were obtained the compounds shown in Table 10.

TABLE 10

| $R^1$ | $R^2$ | X | Melting point, °C. | Recrystallizing solvent | Yield % |
|---|---|---|---|---|---|
| CH$_3$ | H | S | 75.5–76.5 | Ether-hexane | 57.7 |
|  | H | S | 90–91 | Ether-hexane | 67.8 |
| 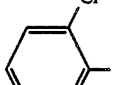 | C$_2$H$_5$ | O | 128.5–130 | Ether-hexane | 65.8 |
| 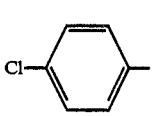 | CH$_3$ | O | 105–106 | Ether | 59.6 |
| 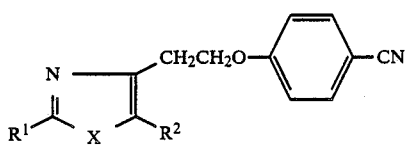 | CH$_3$ | O | 134–135 | Ether-hexane | 74.9 |

TABLE 10-continued

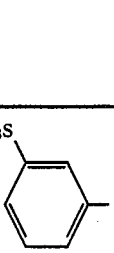

| $R^1$ | $R^2$ | X | Melting point, °C. | Recrystallizing solvent | Yield % |
|---|---|---|---|---|---|
| 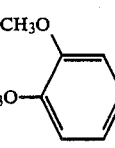 | CH$_3$ | O | 110–111.5 | Ether-hexane | 83.1 |
|  | CH$_3$ | O | 128–129 | Acetone-hexane | 90.3 |
| 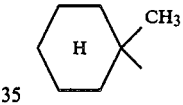 | CH$_3$ | O | 89–91 | Ether-hexane | 74.8 |
| 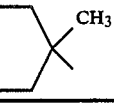 | CH$_3$ | O | Oily material | — | 59.7 |
|  | CH$_3$ | O | Oily material | — | 42.6 |

REFERENCE EXAMPLE 22

A mixture of 4-[2-(5-methyl-2-phenyl-4-oxazolyl)ethoxy]benzonitrile (6.5 g), Raney nickel alloy (6.5 g) and 70% formic acid (100 ml) was heated under reflux for 2 hours. The insoluble matter was filtered off, and the filtrate was concentrated under reduced pressure. Water was added to the residue, and the mixture was extracted with ethyl acetate. The ethyl acetate layer was washed with water, dried (MgSO$_4$) and concentrated. The remaining oily material was chromatographed on a column of silica gel, and from the fractions eluted with chloroform-hexane (1:1, V/V), there were obtained crystlas (5.2 g, 78.5%) of 4-[2-(5-methyl-2-phenyl-4-oxazolyl)ethoxy]benzaldehyde. Recrystallization from ether-hexane yielded colorless needles, m.p. 82°–84° C. Elemental analysis for $C_{19}H_{17}NO_3$; Calcd.: C, 74.25; H, 5.57; N, 4.56. Found: C, 74.47; H, 5.53; N, 4.34.

By a procedure similar to the above, there were obtained the compounds shown in Table 11.

TABLE 11

Structure: R¹-C(=N)-X-C(R²)=C-(CH)$_m$-(CH$_2$)$_n$-O-C$_6$H$_4$-CHO with OH on the (CH)$_m$ carbon

| R¹ | R² | X | m | n | Melting point, °C. | Recrystallizing solvent | Yield % |
|---|---|---|---|---|---|---|---|
| CH₃ | H | S | 0 | 2 | 69–70 | Ether-hexane | 75.5 |
| phenyl | H | S | 0 | 2 | 60–61 | Ether-hexane | 71.4 |
| phenyl | C₂H₅ | O | 0 | 2 | Oily material | — | 85.2 |
| 2-chlorophenyl | CH₃ | O | 0 | 2 | 74–75 | Ether-hexane | 81.0 |
| 4-chlorophenyl | CH₃ | O | 0 | 2 | 113–114 | Ether-hexane | 59.5 |
| 3-(methylthio)phenyl | CH₃ | O | 0 | 2 | 81–82 | Ether-hexane | 54.5 |
| 3,4-dimethoxyphenyl | CH₃ | O | 0 | 2 | 85–89 | Ether | 70.3 |
| 2-thienyl | CH₃ | O | 0 | 2 | Oily material | — | 95.5 |
| 1-methylcyclohexyl | CH₃ | O | 0 | 2 | 75–76 | Ether-hexane | 80.6 |
| 1-methylcyclohexenyl | CH₃ | O | 0 | 2 | Oily material | — | 68.2 |
| phenyl | CH₃ | O | 1 | 1 | 136–137 | Acetone | 71.1 |

REFERENCE EXAMPLE 23

A mixture of 4-chloromethyl-5-methyl-2-phenyloxazole (3.12 g), 4-hydroxybenzaldehyde (1.83 g), potassium carbonate (2.28 g) and dimethylformaide (40 ml) was stirred under heating at 110° C. for 1 hour. The reaction solution was poured into ice-cold water, and the crystals which separated out were collected by filtration to give 4-(5-methyl-2-phenyl-4-oxazolyl)methoxybenzaldehyde (4.40 g, 99.8%). Recrystallization from ether-hexane yielded colorless prisms, m.p. 112°–113° C. Elemental analysis for $C_{18}H_{15}NO_3$; Calcd.: C, 73.71; H, 5.15; N, 4.87. Found: C, 73.87; H, 5.26; N, 4.81.

By a procedure similar to the above, there were obtained the compounds shown in Table 12.

TABLE 12

(Structure shown: oxazole/thiazole with $R^1$, $R^2$, X, and $(CO)_mCH_2O$–phenyl–CHO substituents)

| $R^1$ | $R^2$ | X | m | Melting point, °C. | Recrystallizing solvent | Yield % |
|---|---|---|---|---|---|---|
| phenyl | H | S | 0 | 88–89 | Ether-hexane | 94.7 |
| phenyl | H | O | 0 | 99.5–100.5 | Acetone-hexane | 88.7 |
| phenyl | $CH_3$ | O | 1 | 175–177 | Chloroform-ethanol | 80.4 |
| $CH_3$ | $CH_3$ | O | 1 | 130.5–132 | Ethanol | 94.3 |

REFERENCE EXAMPLE 24

A mixture of 4-bromoacetyl-5-methyl-2-phenyloxazole (7.0 g), p-cyanophenol (3.0 g), potassium carbonate (6.9 g) and methyl ethyl ketone (100 ml) was heated under reflux for 2 hours. The reaction mixture was concentrated under reduced pressure, and water (100 ml)-ether (100 ml) was added to the residue. The mixture was stirred, and the crystals were collected by filtration. Recrystallization from chloroform-ethanol afforded 4-[2-(5-methyl-2-phenyl-4-oxazolyl)-2-oxoethoxy]benzonitrile (6.3 g, 78.8%), as brownish prisms, m.p. 202°–203° C.

REFERENCE EXAMPLE 25

Sodium borohydride (0.654 mg) was added to a suspension of 4-[2-(5-methyl-2-phenyl-4-oxazolyl)-2-oxoethoxy]benzonitrile (5.5 g) in methanol (100 ml)-N,N-dimethylformamide (50 ml), followed by stirring at room temperature for 1 hour. The reaction solution was poured into water and the crystals which separated out were collected by filtration to give 4-[2-hydroxy-2-(5-methyl-phenyl-4-oxazolyl)ethoxy]benzonitrile (5.1 g, 92.7%). Recrystallization from acetone afforded colorless neddles, m.p. 176°–177° C.

EXPERIMENT EXAMPLE

Blood glucose and plasma lipid lowering actions in mice:

Test compounds were given to KKAy-mice (male, 8 to 10 week old, groups of 5 mice each) as a dietary admixture of 0.001% or 0.005% in CE-2 powdered diet (CLEA Japan Inc., Tokyo) for 4 days. The animals were allowed free access to diet and water. Blood samples were taken from the orbital venous plexuses of the mice. Blood glucose was measured by a glucose oxidase method and plasma triglyceride (TG) was enzymatically determined using a commercially available assay kit, Cleantech TG-S kit (Iatron). The respective measurements were used for calculation in accordance with the following equation. The results are shown in Table 13, in which the data obtained with a known compound having similar chemical structure are given for comparison.

TABLE 13

$$\frac{\left(\begin{array}{c}\text{measurement for the}\\\text{control group}\end{array}\right) - \left(\begin{array}{c}\text{measurement for}\\\text{the treated group}\end{array}\right)}{\left(\begin{array}{c}\text{measurement for the}\\\text{control group}\end{array}\right)} \times 100$$

| Compound (Example No.) | Blood-glucose lowering action (%) | | TG lowering action (%) | |
|---|---|---|---|---|
| | 0.001% | 0.005% | 0.001% | 0.005% |
| 1 | — | 48**** | — | 51*** |
| 2 | — | 28*** | — | 32* |
| 6 | 23*** | 41**** | 17** | 44**** |
| 7 | — | 25** | — | 30** |
| 8 | — | 21** | — | 35* |
| 12 | 55**** | 59**** | 67**** | 66**** |
| 14 | — | 42*** | — | 52*** |
| 15 | — | 37*** | — | 42*** |
| 16 | 39**** | 52**** | 54*** | 63*** |
| 17 | 41**** | 58**** | 51** | 68*** |
| 18 | — | 55**** | — | 56**** |
| 19 | — | 52**** | — | 65**** |
| 20 | — | 55**** | — | 37*** |
| 21 | — | 56**** | — | 45 |
| 22 | 54**** | 58**** | 62**** | 81**** |
| 23 | 49**** | 55**** | 55**** | 79**** |
| 24 | 53**** | 55**** | 63**** | 72**** |
| 25 | — | 46**** | — | 45*** |
| 26 | 50**** | 50**** | 41**** | 69**** |
| 27 | 50**** | 51**** | 41**** | 72**** |
| 28 | 55**** | 51**** | 52**** | 62**** |
| 34 | 21*** | 53**** | 23 | 54**** |
| 37 | 51**** | 52**** | 58**** | 71**** |
| 47 | 50**** | 55**** | 65**** | 67**** |
| 50 | 41**** | 57**** | 41*** | 57**** |
| 52 | — | 54**** | — | 59**** |
| 53 | — | 31**** | — | 30** |
| 55 | — | 52**** | — | 58**** |
| 57 | — | 55**** | — | 57**** |
| 58 | — | 33* | — | 29 |
| 59 | 36**** | 56**** | 54*** | 60**** |
| 63 | — | 66**** | — | 51**** |
| 64 | 26**** | 59**** | 37* | 61**** |
| Control compound: Ciglitazone[1] | — | 10 | — | −13 | t-test; *P 0.05, P 0.02, *P 0.01, ****P 0.001
[1]5-[4-(1-Methylcyclohexylmethxoy)]benzyl-2,4-thiazolidinedione.

[Results]

As is obvious from Table 13, the compounds of this invention demonstrated statistically significant blood-glucose or/and TG lowering actions, whereas the control compound, at the dose employed in this experiment, failed to exhibit any significant action.

| Tablet Production Example | |
|---|---|
| (a) (1) 5-{4-[2-(5-methyl-2-phenyl-4-oxazolyl)-ethoxy]benzyl}-2,4-thiazolidinedione | 10 g |
| (2) Lactose | 50 g |
| (3) Corn starch | 15 g |
| (4) Carboxymethylcellulose calcium | 44 g |
| (5) Magnesium stearate | 1 g |
| | 120 g |

-continued

| Tablet Production Example | |
|---|---|
| | for 1000 tablets |

The whole amount each of the ingredients (1), (2) and (3) as well as 30 g of the ingredient (4) are kneaded with water, and the mixture was dried under vacuum and granulated. The resulting granules are mixed with 14 g of the ingredient (4) and 1 g of the ingredient (5), and the mixture is compressed into tablets by a tabletting machine to prepare 1000 tablets each containing 10 mg of the ingredient (1).

| (b) | (1) 5-{4-[2-(5-Methyl-2-phenyl-4-oxazolyl)-ethoxy]benzylidene}-2,4-thiazolidinedione | 30 g |
|---|---|---|
| | (2) Lactose | 50 g |
| | (3) Corn starch | 15 g |
| | (4) Carboxymethylcellulose calcium | 44 g |
| | (5) Magnesium stearate | 1 g |
| | | 140 g |
| | | for 1000 tablets |

The whole amount each of the ingredients (1), (2) and (3) as well as 30 g of the ingredient (4) are kneaded with water, and the mixture is dried under vacuum and granulated. The resulting granules are mixed with 14 g of the ingredient (4) and 1 g of the ingredient (5), and the mixture is compressed into tablets by a tabletting machine to prepare 1000 tablets each containing 30 mg of the ingredient (1).

What is claimed is:

1. A compound of the formula:

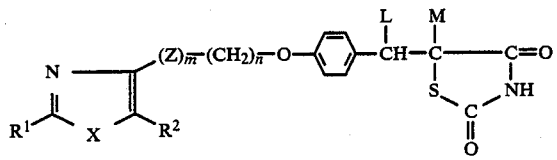

wherein $R^1$ is hydrogen, a hydrocarbon residue having 1 to 13 carbon atoms or a five- or six-membered ring containing, in addition to carbon, 1 to 3 atoms selected from N, O and S as a ring-forming atom and capable of bonding through carbon, and each of said hydrocarbon residue and said ring may be substituted by 1 to 3 substituents selected from the group consisting of alkyl having 1 to 3 carbon atoms when $R^1$ includes an alicyclic group or is a saturated heterocyclic group, or by 1 to 4 substituents selected from the group consisting of halogen, hydroxyl, cyano, trifluoromethyl, alkoxy having 1 to 4 carbon atoms, alkyl having 1 to 4 carbon atoms, alkoxycarbonyl having 2 to 4 carbon atoms and alkylthio having 1 to 3 carbon atoms when either $R^1$ includes aromatic hydrocarbon or $R^1$ is a heteroaromatic ring group; $R^2$ is hydrogen or lower alkyl which may be substituted by hydroxyl; X is an oxygen or sulfur atom; Z is a hydroxylated methylene or carbonyl; m is 0 or 1; n is an integer of 1 to 3; and L and M represent independently a hydrogen atom or L and M combine with each other to cooperate jointly to form a linkage,
or a pharmaceutically acceptable salt thereof.

2. A compound as claimed in claim 1, wherein the hydrocarbon residue represented by $R^1$ is an aliphatic hydrocarbon residue, an alicyclic hydrocarbon residue, an alicyclic-aliphatic hydrocarbon residue, an aromatic-aliphatic hydrocarbon residue or an aromatic hydrocarbon residue.

3. A compound as claimed in claim 1, wherein the ring represented by $R^1$ is a heteroaromatic ring group or a saturated heterocyclic group.

4. A compound as claimed in claim 1, wherein $R^1$ is an alicyclic hydrocarbon residue, an alicyclic-aliphatic hydrocarbon residue or a saturated heterocyclic group, each of which may be substituted by alkyl of 1 to 3 carbon atoms.

5. A compound as claimed in claim 1, wherein $R^1$ is an aromatic-aliphatic hydrocarbon residue, aromatic hydrocarbon residue or heteroaromatic ring group, each of which may be substituted by halogen, hydroxyl, cyano, trifluoromethyl, alkoxy having 1 to 4 carbon atoms, alkyl having 1 to 4 carbon atoms, alkoxycarbonyl having 2 to 4 carbon atoms or alkylthio having 1 to 3 carbon atoms.

6. A compound as claimed in claim 1, wherein $R^2$ is alkyl having 1 to 5 carbon atoms.

7. A compound as claimed in claim 1, wherein m is 1 and Z is hydroxymethylene.

8. A compound as claimed in claim 1, wherein the compound is 5-{4-[2-(5-methyl-2-phenyl-4-oxazolyl)ethoxy]benzylidene}-2,4-thiazolidinedione.

9. A compound as claimed in claim 1, wherein the compound is 5-{4-[2-(5-methyl-2-phenyl-4-oxazolyl)-2-hydroxyethoxy]benzyl}-2,4-thiazolidinedione.

10. A compound as claimed in claim 1, wherein the compound is 5-{4-[2-(5-methyl-2-phenyl-4-oxazolyl)ethoxy]benzyl}-2,4-thiazolidinedione.

11. A pharmaceutical composition which contains a thiazolidinedione derivative of the formula:

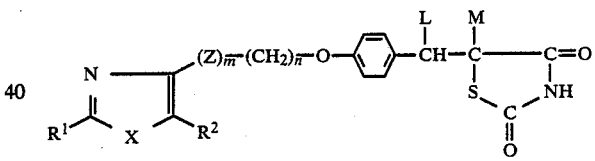

wherein $R^1$ is hydrogen, a hydrocarbon residue having 1 to 13 carbon atoms or a five- or six-membered ring containing, in addition to carbon, 1 to 3 atoms selected from N, O and S as a ring-forming atom and capable of bonding through carbon, and each of said hydrocarbon residue and said ring may be substituted by 1 to 3 substituents selected from the group consisting of alkyl having 1 to 3 carbon atoms when $R^1$ includes an alicyclic group or is a saturated heterocyclic group, or by 1 to 4 substituents selected from the group consisting of halogen, hydroxyl, cyano, trifluoromethyl, alkoxy having 1 to 4 carbon atoms, alkyl having 1 to 4 carbon atoms, alkoxycarbonyl having 2 to 4 carbon atoms and alkylthio having 1 to 3 carbon atoms when either $R^1$ includes aromatic hydrocarbon or $R^1$ is a heteroaromatic ring group; $R^2$ is hydrogen or lower alkyl which may be substituted by hydroxyl; X is an oxygen or sulfur atom; Z is a hydroxylated methylene or carbonyl; m is 0 or 1; n is an integer of 1 to 3; and L and M represent independently a hydrogen atom or L and M combine with each other to cooperate jointly to form a linkage,
or a pharmaceutically acceptable salt thereof,
and a pharmaceutically acceptable carrier therefor.

12. A method for the treatment of diabetes or hyperlipemia, which comprises administering to a mammal suffering from diabetes or hyperlipemia a compound of the formula:

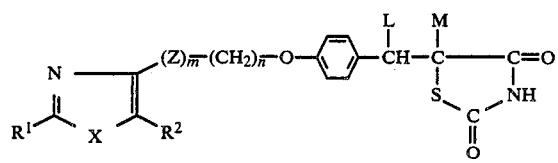

wherein $R^1$ is hydrogen, a hydrocarbon residue having 1 to 13 carbon atoms or a five- or six-membered ring containing, in addition to carbon, 1 to 3 atoms selected from N, O and S as a ring-forming atom and capable of bonding through carbon, and each of said hydrocarbon residue and said ring may be substituted by 1 to 3 substituents selected from the group consisting of alkyl having 1 to 3 carbon atoms when $R^1$ includes an alicyclic group or is a saturated heterocyclic group, or by 1 to 4 substituents selected from the group consisting of halogen, hydroxyl, cyano, trifluoromethyl, alkoxy having 1 to 4 carbon atoms, alkyl having 1 to 4 carbon atoms, alkoxycarbonyl having 2 to 4 carbon atoms and alkylthio having 1 to 3 carbon atoms when either $R^1$ includes aromatic hydrocarbon or $R^1$ is a heteroaromatic ring group; $R^2$ is hydrogen or lower alkyl which may be substituted by hydroxyl; X is an oxygen or sulfur atom; Z is a hydroxylated methylene or carbonyl; m is 0 or 1; n is an integer of 1 to 3; and L and M represent independently a hydrogen atom or L and M combine with each other to cooperate jointly to form a linkage, or a pharmaceutically acceptable salt thereof, in a therapeutically effective amount of about 0.001 to 10 mg per kilogram of body weight of the mammal per day.

* * * * *